(12) United States Patent
Vande Woude et al.

(10) Patent No.: US 7,968,762 B2
(45) Date of Patent: Jun. 28, 2011

(54) IMMUNE-COMPROMISED TRANSGENIC MICE EXPRESSING HUMAN HEPATOCYTE GROWTH FACTOR (HHGF)

(75) Inventors: George F. Vande Woude, Ada, MI (US); Yu-wen Zhang, Grand Rapids, MI (US); Nariyoshi Shinomiya, Saitama (JP)

(73) Assignee: Van Andel Research Institute, Grand Rapids, MI (US)

( * ) Notice: Subject to any disclaimer, the term of this patent is extended or adjusted under 35 U.S.C. 154(b) by 302 days.

(21) Appl. No.: 11/571,947

(22) PCT Filed: Jul. 12, 2005

(86) PCT No.: PCT/US2005/024788
§ 371 (c)(1),
(2), (4) Date: Feb. 18, 2008

(87) PCT Pub. No.: WO2006/017322
PCT Pub. Date: Feb. 16, 2006

(65) Prior Publication Data
US 2008/0196110 A1 Aug. 14, 2008

Related U.S. Application Data

(60) Provisional application No. 60/587,044, filed on Jul. 13, 2004.

(51) Int. Cl.
*A01K 67/027* (2006.01)
*A01K 67/00* (2006.01)
*A01K 67/033* (2006.01)
*G01N 33/00* (2006.01)
*C12N 15/00* (2006.01)

(52) U.S. Cl. ............ 800/18; 800/3; 800/9; 800/10; 800/13; 800/14; 800/21

(58) Field of Classification Search .................. None
See application file for complete search history.

(56) References Cited

U.S. PATENT DOCUMENTS

| | | | |
|---|---|---|---|
| 4,736,866 A | 4/1988 | Leder | |
| 4,870,009 A | 9/1989 | Evans | |
| 4,873,191 A | 10/1989 | Wagner | |
| 4,946,778 A | 8/1990 | Ladner | |
| 5,378,825 A | 1/1995 | Cook | |
| 5,530,179 A | 6/1996 | Terhorst | |
| 5,550,316 A | 8/1996 | Mintz | |
| 5,602,309 A | 2/1997 | Albers | |
| 5,643,551 A | 7/1997 | Namikawa | |
| 5,840,708 A | 11/1998 | Weiss | |
| 5,859,310 A * | 1/1999 | Bujard et al. | 800/9 |
| 5,871,959 A * | 2/1999 | Rong et al. | 435/69.1 |
| 5,885,970 A | 3/1999 | Bennett | |
| 5,891,725 A | 4/1999 | Soreq | |
| 5,925,803 A | 7/1999 | Leder | |
| 5,998,383 A | 12/1999 | Wright | |
| 6,005,095 A | 12/1999 | Capaccioli | |
| 6,040,296 A | 3/2000 | Nyce | |
| 6,087,343 A | 7/2000 | Phillips | |
| 6,096,722 A | 8/2000 | Bennett | |
| 6,107,540 A | 8/2000 | Sawyer | |
| 6,117,847 A | 9/2000 | Bennett | |
| 6,133,246 A | 10/2000 | McKay | |
| 6,150,162 A | 11/2000 | Bennett | |
| 6,153,595 A | 11/2000 | Draper | |
| 6,168,950 B1 | 1/2001 | Monia | |
| 6,187,587 B1 | 2/2001 | Popoff | |
| 6,190,661 B1 | 2/2001 | Kelley | |
| 6,190,869 B1 | 2/2001 | Bennett | |
| 6,197,584 B1 | 3/2001 | Bennett | |
| 6,200,807 B1 | 3/2001 | Bennett | |
| 6,200,960 B1 | 3/2001 | Khachigian | |
| 6,222,094 B1 | 4/2001 | Hansson | |
| 6,323,390 B1 | 11/2001 | Wu | |
| 6,355,415 B1 | 3/2002 | Wagner | |
| 6,455,280 B1 * | 9/2002 | Edwards et al. | 435/69.1 |
| 6,506,559 B1 | 1/2003 | Fire | |
| 6,872,868 B1 | 3/2005 | Wagner | |
| 2003/0206887 A1 | 11/2003 | Morrissey | |

FOREIGN PATENT DOCUMENTS

| | | |
|---|---|---|
| WO | 88-00239 A1 | 1/1988 |
| WO | 88-04300 A1 | 6/1988 |
| WO | 90-05188 A1 | 5/1990 |
| WO | 92-11757 A1 | 7/1992 |
| WO | 94-18317 A1 | 8/1994 |
| WO | 95-02684 A1 | 1/1995 |
| WO | 95-05389 A1 | 2/1995 |
| WO | WO 95/05736 * | 3/1995 |
| WO | 99-07409 A1 | 2/1999 |
| WO | 99-32619 A1 | 7/1999 |
| WO | 00-01846 A2 | 1/2000 |
| WO | 00-44895 A1 | 8/2000 |
| WO | 00-44914 A1 | 8/2000 |
| WO | 01-29058 A1 | 4/2001 |
| WO | 01-36646 A1 | 5/2001 |
| WO | 01-75164 A2 | 10/2001 |

(Continued)

OTHER PUBLICATIONS

Pilewski et al., 2001, Am. J. Respir. Cell Mol. Biol., 24: 556-562.*

(Continued)

*Primary Examiner* — Joanne Hama
(74) *Attorney, Agent, or Firm* — Price, Heneveld, Cooper, DeWitt & Litton, LLP

(57) ABSTRACT

A transgenic animal model for evaluating growth, survival and/or metastasis of xenotransplanted normal or tumor cells or tissue is disclosed, in which a human growth factor, hHGF stimulates growth in vivo of human cells or tissue. A strain of Tg mice on the C3H background that is immunocompromised as a result of a homozygous scid gene has been bred which express a nucleic acid encoding hHGF/SE The ectopically expressed hHGF/SF ligand significantly enhances growth of human tumor cell lines and explanted tumor cells or tissue that express the Met receptor for hHGF. Such animals also have an enlarged normal livers and greater than normal liver regenerative capacity. Any Met-expressing hHGF-dependent human cells, including hepatocytes and various stem cells can survive and grow in such animals.

32 Claims, 15 Drawing Sheets

FOREIGN PATENT DOCUMENTS

| | | |
|---|---|---|
| WO | 01-89304 A1 | 11/2001 |
| WO | 01-90401 A2 | 11/2001 |
| WO | 01-92513 A1 | 12/2001 |
| WO | 02-16620 A2 | 2/2002 |
| WO | 02-29858 A2 | 4/2002 |
| WO | 03-057155 A2 | 7/2003 |

OTHER PUBLICATIONS

Takayama et al., 1997, PNAS, USA, 94: 701-706.*
Johansen et al., 1990, FEBS 267:289-294.*
Capetanaki et al., 1989, The Journal of Cell Biology, 109: 1653-1664.*
Maulik et al., 2002, Cytokine and Growth Factor Reviews, 13: 41-59.*
Yu et al., "Constitutive c-Met Signaling through a Nonautocrine Mechanism Promotes Metastasis in a Transgenic Transplantation Model," Cancer Research, May 2002, vol. 62, pp. 2951-2956.
Jahner, D., Haase, K., Mulligan, R., & Jaenisch, R., Insertion of the bacterial gpt gene into the germ line of mice by retroviral infection. Proc Natl Acad Sci U S A 82 (20), 6927-6931 (1985).
Jeffers, M. et al., The mutationally activated Met receptor mediates motility and metastasis. Proc Natl Acad Sci U S A 95 (24), 14417-14422 (1998).
Jeffers, M., Rong, S., & Vande Woude, G.F., Enhanced tumorigenicity and invasion-metastasis by hepatocyte growth factor/scatter factor-met signalling in human cells concomitant with induction of the urokinase proteolysis network. Mol Cell Biol 16 (3), 1115-1125 (1996).
Jenuwein, T., Molecular biology. An RNA-guided pathway for the epigenome. Science 297 (5590), 2215-2218 (2002).
Karlin, S. & Altschul, S.F., Applications and statistics for multiple high-scoring segments in molecular sequences. Proc Natl Acad Sci U S A 90 (12), 5873-5877 (1993).
Kawasaki, H. & Taira, K., Short hairpin type of dsRNAs that are controlled by tRNA(Val) promoter significantly induce RNAi-mediated gene silencing in the cytoplasm of human cells. Nucleic Acids Res 31 (2), 700-707 (2003).
Kerbel, R.S., Human tumor xenografts as predictive preclinical models for anticancer drug activity in humans: better than commonly perceived-but they can be improved. Cancer Biol Ther 2 (4 Suppl 1), S134-139 (2003).
Kohler, G. & Milstein, C., Continuous cultures of fused cells secreting antibody of predefined specificity. Nature 256 (5517), 495-497 (1975).
Kollias, G., Wrighton, N., Hurst, J., & Grosveld, F., Regulated expression of human A gamma-, beta-, and hybrid gamma beta-globin genes in transgenic mice: manipulation of the developmental expression patterns. Cell 46 (1), 89-94 (1986).
Kozbor, D., et al., 1983, The production of Monoclonal Antibodies from human Lymphocytes. Immunol Today 4:72.
Lacy, E., Roberts, S., Evans, E.P., Burtenshaw, M.D., & Costantini, F.D., A foreign beta-globin gene in transgenic mice: integration at abnormal chromosomal positions and expression in inappropriate tissues. Cell 34 (2), 343-358 (1983).
Landegren, U., Kaiser, R., Sanders, J., & Hood, L., A ligase-mediated gene detection technique. Science 241 (4869), 1077-1080 (1988).
Lau, N.C. & Bartel, D.P., Censors of the genome. Sci Am 289 (2), 34-41 (2003).
Lee, J.S., Johnson, D.A., & Morgan, A.R., Complexes formed by (pyrimidine)n . (purine)n DNAs on lowering the pH are three-stranded. Nucleic Acids Res 6 (9), 3073-3091 (1979).
Lee, N.S. et al., Expression of small interfering RNAs targeted against HIV-1 rev transcripts in human cells. Nat Biotechnol 20 (5), 500-505 (2002).
Marasco, W.A., Intrabodies: turning the humoral immune system outside in for intracellular immunization. Gene Ther 4 (1), 11-15 (1997).
McGrory, W.J., Bautista, D.S., & Graham, F.L., A simple technique for the rescue of early region I mutations into infectious human adenovirus type 5. Virology 163 (2), 614-617 (1988).
McKnight, G.S., Hammer, R.E., Kuenzel, E.A., & Brinster, R.L., Expression of the chicken transferrin gene in transgenic mice. Cell 34 (2), 335-341 (1983).
McManus, M.T. & Sharp, P.A., Gene silencing in mammals by small interfering RNAs. Nat Rev Genet 3 (10), 737-747 (2002).
McManus, M.T., Petersen, C.P., Haines, B.B., Chen, J., & Sharp, P.A., Gene silencing using micro-RNA designed hairpins. RNA 8 (6), 842-850 (2002).
Miyagishi et al. U6 promotor-driven siRNAs with four uridine 3' overhangs efficiently suppress targeted gene expression in mammalian cells. Nature Biotechnol 20, 497-500 (2003).
Moss et al., RNA interference: It's a small RNA world. Curr Biol. 11:R772-5 (2001).
Mueller, B.M. & Reisfeld, R.A., Potential of the scid mouse as a host for human tumors. Cancer Metastasis Rev 10 (3), 193-200 (1991).
Nakazawa, H. et al., UV and skin cancer: Specific p53 gene mutation in normal skin as a biologically relevant exposure measurement. Proc Natl Acad Sci U S A 91 (1), 360-364 (1994).
Okano, H., Aruga, J., Nakagawa, T., Shiota, C., & Mikoshiba, K., Myelin basic protein gene and the function of antisense RNA in its repression in myelin-deficient mutant mouse. J Neurochem 56 (2), 560-567 (1991).
Paddison, P.J., Caudy, A.A., & Hannon, G.J., Stable suppression of gene expression by RNAi in mammalian cells. Proc Natl Acad Sci U S A 99 (3), 1443-1448 (2002).
Paddison, P.J., Caudy, A.A., Bernstein, E., Hannon, G.J., & Conklin, D.S., Short hairpin RNAs (shRNAs) induce sequence-specific silencing in mammalian cells. Genes Dev 16 (8), 948-958 (2002).
Palmiter, R.D. et al., Dramatic growth of mice that develop from eggs microinjected with metallothionein-growth hormone fusion genes. Nature 300 (5893), 611-615 (1982).
Palmiter, R.D., Chen, H.Y., & Brinster, R.L., Differential regulation of metallothionein-thymidine kinase fusion genes in transgenic mice and their offspring. Cell 29 (2), 701-710 (1982).
Palmiter, R.D., Norstedt, G., Gelinas, R.E., Hammer, R.E., & Brinster, R.L., Metallothionein-human GH fusion genes stimulate growth of mice. Science 222 (4625), 809-814 (1983).
Paul, C.P., Good, P.D., Winer, I., & Engelke, D.R., Effective expression of small interfering RNA in human cells. Nat Biotechnol 20 (5), 505-508 (2002).
Pearson, W.R. & Lipman, D.J., Improved tools for biological sequence comparison. Proc Natl Acad Sci U S A 85 (8), 2444-2448 (1988).
Reinhart, B.J. & Bartel, D.P., Small RNAs correspond to centromere heterochromatic repeats. Science 297 (5588), 1831 (2002).
Reinhart, B.J., Weinstein, E.G., Rhoades, M.W., Bartel, B., & Bartel, D.P., MicroRNAs in plants. Genes Dev 16 (13), 1616-1626 (2002).
Robertson, E., Bradley, A., Kuehn, M., & Evans, M., Germ-line transmission of genes introduced into cultured pluripotential cells by retroviral vector. Nature 323 (6087), 445-448 (1986).
Rong, S. et al., Tumorigenesis induced by coexpression of human hepatocyte growth factor and the human met protooncogene leads to high levels of expression of the ligand and receptor. Cell Growth Differ 4 (7), 563-569 (1993).
Rong, S. et al., Tumorigenicity of the met proto-oncogene and the gene for hepatocyte growth factor. Mol Cell Biol 12 (11), 5152-5158 (1992).
Sakata, H. et al., Hepatocyte growth factor/scatter factor overexpression induces growth, abnormal development, and tumor formation in transgenic mouse livers. Cell Growth Differ 7 (11), 1513-1523 (1996).
Sedivy et al. Gene Targeting, W.H. Freeman and Company, N.Y., 1992, pp. 123-142.
Shani, M., Tissue-specific and developmentally regulated expression of a chimeric actin-globin gene in transgenic mice. Mol Cell Biol 6 (7), 2624-2631 (1986).
Spencer, D.M., Wandless, T.J., Schreiber, S.L., & Crabtree, G.R., Controlling signal transduction with synthetic ligands. Science 262 (5136), 1019-1024 (1993).
Steward, T.A., Wagner, E.F., & Mintz, B., Human beta-globin gene sequences injected into mouse eggs, retained in adults, and transmitted to progeny. Science 217 (4564), 1046-1048 (1982).
Stewart, C.L., Schuetze, S., Vanek, M., & Wagner, E.F., Expression of retroviral vectors in transgenic mice obtained by embryo infection. EMBO J 6 (2), 383-388 (1987).

Sui, G. et al., A DNA vector-based RNAi technology to suppress gene expression in mammalian cells. Proc Natl Acad Sci U S A 99 (8), 5515-5520 (2002).

Torelli, A. & Robotti, C.A., Advance and Adam: two algorithms for the analysis of global similarity between homologous informational sequences. Comput Appl Biosci 10 (1), 3-5 (1994).

Townes, T.M., Lingrel, J.B., Chen, H.Y., Brinster, R.L., & Palmiter, R.D., Erythroid-specific expression of human beta-globin genes in transgenic mice. EMBO J 4 (7), 1715-1723 (1985).

Travis, J., Making molecular matches in the cell. Science 262 (5136), 989 (1993).

Trusolino, L. & Comoglio, P.M., Scatter-factor and semaphorin receptors: cell signalling for invasive growth. Nat Rev Cancer 2 (4), 289-300 (2002).

Tuschl, T., Zamore, P.D., Lehmann, R., Bartel, D.P., & Sharp, P.A., Targeted mRNA degradation by double-stranded RNA in vitro. Genes Dev 13 (24), 3191-3197 (1999).

Van Der Putten, H. et al., Efficient insertion of genes into the mouse germ line via retroviral vectors. Proc Natl Acad Sci U S A 82 (18), 6148-6152 (1985).

Abounader, R. et al., In vivo targeting of SF/HGF and c-met expression via U1snRNA/ribozymes inhibits glioma growth and angiogenesis and promotes apoptosis. FASEB J 16 (1), 108-110 (2002).

Allshire, R., Molecular biology. RNAi and heterochromatin—a hushed-up affair. Science 297 (5588), 1818-1819 (2002).

Altschul, S.F. et al., Gapped BLAST and PSI-BLAST: a new generation of protein database search programs. Nucleic Acids Res 25 (17), 3389-3402 (1997).

Atabey, N. et al., Potent blockade of hepatocyte growth factor-stimulated cell motility, matrix invasion and branching morphogenesis by antagonists of Grb2 Src homology 2 domain interactions. J Biol Chem 276 (17), 14308-14314 (2001).

Bankert, R.B., Hess, S.D., & Egilmez, N.K., SCID mouse models to study human cancer pathogenesis and approaches to therapy: potential, limitations, and future directions. Front Biosci 7, 45-62 (2002).

Bass, B.L., RNA interference. The short answer. Nature 411 (6836), 428-429 (2001).

Beal, P.A. & Dervan, P.B., Second structural motif for recognition of DNA by oligonucleotide-directed triple-helix formation. Science 251 (4999), 1360-1363 (1991).

Been, M.D. & Cech, T.R., One binding site determines sequence specificity of Tetrahymena pre-rRNA self-splicing, trans-splicing, and RNA enzyme activity. Cell 47 (2), 207-216 (1986).

Bernstein et al. The rest is silence. RNA 7:1509-1521 (2001).

Bhargava, M. et al., Scatter factor and hepatocyte growth factor: activities, properties, and mechanism. Cell Growth Differ 3 (1), 11-20 (1992).

Birchmeier, C., Birchmeier, W., Gherardi, E., & Vande Woude, G.F., Met, metastasis, motility and more. Nat Rev Mol Cell Biol 4 (12), 915-925 (2003).

Bock, T.A., Orlic, D., Dunbar, C.E., Broxmeyer, H.E., & Bodine, D.M., Improved engraftment of human hematopoietic cells in severe combined immunodeficient (SCID) mice carrying human cytokine transgenes. J Exp Med 182 (6), 2037-2043 (1995).

Brach, M.A. et al., Ionizing radiation induces expression and binding activity of the nuclear factor kappa B. J Clin Invest 88 (2), 691-695 (1991).

Bradley, A., Evans, M., Kaufman, M.H., & Robertson, E., Formation of germ-line chimaeras from embryo-derived teratocarcinoma cell lines. Nature 309 (5965), 255-256 (1984).

Braselmann, S., Graninger, P., & Busslinger, M., A selective transcriptional induction system for mammalian cells based on Gal4-estrogen receptor fusion proteins. Proc Natl Acad Sci U S A 90 (5), 1657-1661 (1993).

Brinster, R.L. et al., Expression of a microinjected immunoglobulin gene in the spleen of transgenic mice. Nature 306 (5941), 332-336 (1983).

Brinster, R.L. et al., Somatic expression of herpes thymidine kinase in mice following injection of a fusion gene into eggs. Cell 27 (1 Pt 2), 223-231 (1981).

Brinster, R.L., Chen, H.Y., Trumbauer, M.E., Yagle, M.K., & Palmiter, R.D., Factors affecting the efficiency of introducing foreign DNA into mice by microinjecting eggs. Proc Natl Acad Sci U S A 82 (13), 4438-4442 (1985).

Brummelkamp, T.R., Bernards, R., & Agami, R., A system for stable expression of short interfering RNAs in mammalian cells. Science 296 (5567), 550-553 (2002).

Cao, B. et al., Neutralizing monoclonal antibodies to hepatocyte growth factor/scatter factor (HGF/SF) display antitumor activity in animal models. Proc Natl Acad Sci U S A 98 (13), 7443-7448 (2001).

Chada, K. et al., Specific expression of a foreign beta-globin gene in erythroid cells of transgenic mice. Nature 314 (28), 377-380 (1985).

Chada, K., Magram, J., & Costantini, F., An embryonic pattern of expression of a human fetal globin gene in transgenic mice. Nature 319 (20), 685-689 (1986).

Christensen, J.G. et al., A selective small molecule inhibitor of c-Met kinase inhibits c-Met-dependent phenotypes in vitro and exhibits cytoreductive antitumor activity in vivo. Cancer Res 63 (21), 7345-7355 (2003).

Cole et al., In: Monoclonal Antibodies and Cancer Therapy, Alan R. Liss, Inc., 1985, pp. 77-96.

Cooney, M., Czernuszewicz, G., Postel, E.H., Flint, S.J., & Hogan, M.E., Site-specific oligonucleotide binding represses transcription of the human c-myc gene in vitro. Science 241 (4864), 456-459 (1988).

Costantini, F. & Lacy, E., Introduction of a rabbit beta-globin gene into the mouse germ line. Nature 294 (5836), 92-94 (1981).

Date, K. et al., Inhibition of tumor growth and invasion by a four-kringle antagonist (HGF/NK4) for hepatocyte growth factor. Oncogene 17 (23), 3045-3054 (1998).

Datta, R. et al., Ionizing radiation activates transcription of the EGR1 gene via CArG elements. Proc Natl Acad Sci U S A 89 (21), 10149-10153 (1992).

Devereux, J., Haeberli, P., & Smithies, O., A comprehensive set of sequence analysis programs for the VAX. Nucleic Acids Res 12 (1 Pt 1), 387-395 (1984).

Dykxhoorn, D.M., Novina, C.D., & Sharp, P.A., Killing the messenger: short RNAs that silence gene expression. Nat Rev Mol Cell Biol 4 (6), 457-467 (2003).

Elbashir, S.M. et al., Duplexes of 21-nucleotide RNAs mediate RNA interference in cultured mammalian cells. Nature 411 (6836), 494-498 (2001).

Evans, M.J. & Kaufman, M.H., Establishment in culture of pluripotential cells from mouse embryos. Nature 292 (5819), 154-156 (1981).

Faletto, D.L., Kaplan, D.R., Halverson, D.O., Rosen, E.M., & Vande Woude, G.F., Signal transduction in c-met mediated motogenesis. EXS 65, 107-130 (1993).

Fire, A. et al., Potent and specific genetic interference by double-stranded RNA in Caenorhabditis elegans. Nature 391 (6669), 806-811 (1998).

Firon, M. et al., Dominant negative Met reduces tumorigenicity-metastasis and increases tubule formation in mammary cells. Oncogene 19 (20), 2386-2397 (2000).

Gossen, M. & Bujard, H., Tight control of gene expression in mammalian cells by tetracycline-responsive promoters. Proc Natl Acad Sci U S A 89 (12), 5547-5551 (1992).

Gossler, A., Doetschman, T., Korn, R., Serfling, E., & Kemler, R., Transgenesis by means of blastocyst-derived embryonic stem cell lines. Proc Natl Acad Sci U S A 83 (23), 9065-9069 (1986).

Hall, I.M. et al., Establishment and maintenance of a heterochromatin domain. Science 297 (5590), 2232-2237 (2002).

Hallahan, D.E. et al., Protein kinase C mediates x-ray inducibility of nuclear signal transducers EGR1 and JUN. Proc Natl Acad Sci U S A 88 (6), 2156-2160 (1991).

Hallahan, D.E. et al., Radiation signaling mediated by Jun activation following dissociation from a cell type-specific repressor. J Biol Chem 268 (7), 4903-4907 (1993).

Hallahan, D.E. et al., Spatial and temporal control of gene therapy using ionizing radiation. Nat Med 1 (8), 786-791 (1995).

Hammer, R.E. et al., Production of transgenic rabbits, sheep and pigs by microinjection. Nature 315 (6021), 680-683 (1985).

Hammer, R.E., Krumlauf, R., Camper, S.A., Brinster, R.L., & Tilghman, S.M., Diversity of alpha-fetoprotein gene expression in mice is generated by a combination of separate enhancer elements. Science 235 (4784), 53-58 (1987).

Hannon, G.J., RNA interference. Nature 418 (6894), 244-251 (2002).

Harbers, K., Jahner, D., & Jaenisch, R., Microinjection of cloned retroviral genomes into mouse zygotes: integration and expression in the animal. Nature 293 (5833), 540-542 (1981).

Hutvagner, G. & Zamore, P.D., A microRNA in a multiple-turnover RNAi enzyme complex. Science 297 (5589), 2056-2060 (2002).

Hutvagner, G. & Zamore, P.D., RNAi: nature abhors a double-strand. Curr Opin Genet Dev 12 (2), 225-232 (2002).

Jaenisch, R., Germ line integration and Mendelian transmission of the exogenous Moloney leukemia virus. Proc Natl Acad Sci U S A 73 (4), 1260-1264 (1976).

Jaenisch, R., Transgenic animals. Science 240 (4858), 1468-1474 (1988).

Jahner, D. et al., De novo methylation and expression of retroviral genomes during mouse embryogenesis. Nature 298 (5875), 623-628 (1982).

Volpe, T.A., et al., Regulation of heterochromatic silencing and histone H3 lysine-9 methylation by RNAi. Science 297 (5588), 1833-1837 (2002).

Wagner, et al., The Possibility of Transgenic Livestock. Theriogenology 21, 29-43 (1984).

Otsuka, T et al., "c-Met Autocrine Activation Induces Development of Malignant Melanoma and Acquisition of the Metastatic Phenotype". Cancer Res. 58, No. 22, 5157-5167 (Nov. 15, 1998).

Otsuka, T et al., "Dissociation of Met-Mediated Biological Responses In Vivo: the Natural Hepatocyte Growth Factor/Scatter Factor Splice Variant NK2 Antagonizes Growth but Facilitates Metastasis". Molecular and Cellular Biology 20, No. 6, 2055-2065 (Mar. 2000).

Zhang, Y et al., "Enhanced growth of human met-expressing xenografts in a new strain of immunocompromised mice transgenic for human hepatocyte growth factor/scatter factor". Oncogene 24, 101-106 (2005).

Wagner, E.F., Stewart, T.A., & Mintz, B., The human beta-globin gene and a functional viral thymidine kinase gene in developing mice. Proc Natl Acad Sci U S A 78 (8), 5016-5020 (1981).

Wagner, T.E. et al., Microinjection of a rabbit beta-globin gene into zygotes and its subsequent expression in adult mice and their offspring. Proc Natl Acad Sci U S A 78 (10), 6376-6380 (1981).

Webb, C.P. et al., The geldanamycins are potent inhibitors of the hepatocyte growth factor/scatter factor-met-urokinase plasminogen activator-plasmin proteolytic network. Cancer Res 60 (2), 342-349 (2000).

Weichselbaum, R.R., Hallahan, D., Fuks, Z., & Kufe, D., Radiation induction of immediate early genes: effectors of the radiation-stress response. Int J Radiat Oncol Biol Phys 30 (1), 229-234 (1994).

Weichselbaum, R.R., Hallahan, D.E., Sukhatme, V.P., & Kufe, D.W., Gene therapy targeted by ionizing radiation. Int J Radiat Oncol Biol Phys 24 (3), 565-567 (1992).

Weiss, A., T cell antigen receptor signal transduction: a tale of tails and cytoplasmic protein-tyrosine kinases. Cell 73 (2), 209-212 (1993).

Yu, J.Y., Deruiter, S.L., & Turner, D.L., RNA interference by expression of short-interfering RNAs and hairpin RNAs in mammalian cells. Proc Natl Acad Sci U S A 99 (9), 6047-6052 (2002).

Zaug, A.J. & Cech, T.R., The intervening sequence RNA of Tetrahymena is an enzyme. Science 231 (4737), 470-475 (1986).

Zaug, A.J., Been, M.D., & Cech, T.R., The Tetrahymena ribozyme acts like an RNA restriction endonuclease. Nature 324 (6096), 429-433 (1986).

Zaug, A.J., Kent, J.R., & Cech, T.R., A labile phosphodiester bond at the ligation junction in a circular intervening sequence RNA. Science 224 (4649), 574-578 (1984).

Borman, S., Synthetic Receptors Make It Possible To Turn Genes On and Off at Will. Chem. & Eng. News, Nov. 15, 1993, pp. 55-57.

Simons, J., et al. Gene Transfer into Sheep. Bio/Technology 6, 179-183, 1988.

Coligan et al., in Current Protocols in Immunology, Sec. 2.4.1. (1992).

Coligan et al., in Current Protocols in Immunology, Secs. 2.5.1-2.6.7 (1992).

* cited by examiner

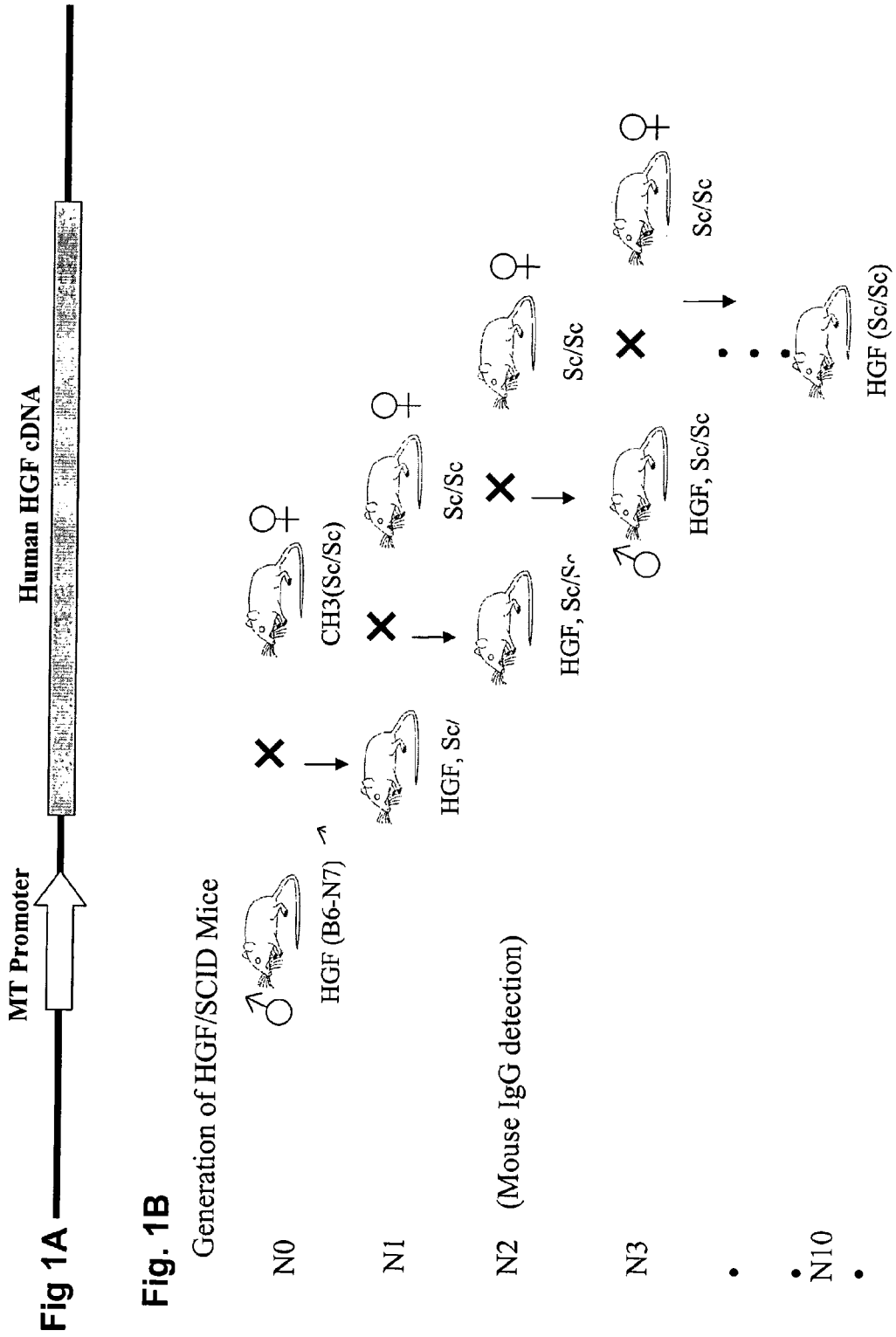

SEQUENCE LISTING

```
<160> NUMBER OF SEQ ID NOS: 9

<210> SEQ ID NO 1
<211> LENGTH: 21
<212> TYPE: DNA
<213> ORGANISM: Artificial Sequence
<220> FEATURE:
<223> OTHER INFORMATION: Primer for hHGF

<400> SEQUENCE: 1
agtctgtgac attcctcagt g                                            21

<210> SEQ ID NO 2
<211> LENGTH: 20
<212> TYPE: DNA
<213> ORGANISM: Artificial Sequence
<220> FEATURE:
<223> OTHER INFORMATION: Primer for hHGF

<400> SEQUENCE: 2
tgagaatccc aacgctgaca                                              20

<210> SEQ ID NO 3
<211> LENGTH: 5898
<212> TYPE: DNA
```

<213> ORGANISM: Homo sapiens

<400> SEQUENCE: 3

```
cacacaacaa acttagctca tcgcaataaa aagcagctca gagccgactg gctcttttag        60
gcactgactc cgaacaggat tctttcaccc aggcatctcc tccagaggga tccgccagcc       120
cgtccagcag caccatgtgg gtgaccaaac tcctgccagc cctgctgctg cagcatgtcc       180
tcctgcatct cctcctgctc cccatcgcca tccctatgc agagggacat aagaaaagaa        240
gaaatacaat tcacgaattc aaaaaatcag caaagactac cctaatcaaa atagatccag       300
cactgaagat aaaaaccaaa aaagtgaata ctgcagacca atgtgctaat agatgtacta       360
ggataatgg acttccattc acttgcaagg cctttgtttt tgataaagcg agaaaacaat        420
gcctctggtt ccccttcaat agcatgtcaa gtggagtgaa gaaagaattt ggccatgaat       480
ttgacctcta tgaaaacaaa gactacatta gaaactgcat catcggtaaa ggacgcagct       540
acaagggaac agtatctatc actaagagtg gcatcaaatg tcagccctgg agttccatga       600
taccacacga acacagcttt ttgccttcga gctatcgggg taaagaccta caggaaaact       660
actgtcgaaa tcctcgaggg gaagaagggg gaccctggtg tttcacaagc aatccagagg       720
tacgctacga agtctgtgac attcctcagt gttcagaagt tgaatgcatg acctgcaatg       780
gggagagtta tcgaggtctc atggatcata cagaatcagg caagatttgt cagcgctggg       840
atcatcagac accacaccgg cacaaattct tgcctgaaag atatcccgac aagggctttg       900
atgataatta ttgccgcaat cccgatggcc agccgaggcc atggtgctat actcttgacc       960
ctcacacccg ctgggagtac tgtgcaatta aaacatgcgc tgacaatact gtaaatgata      1020
ctgatgttcc tatggaaaca actgaatgca tccaaggtca aggagaaggc tacaggggca      1080
ctgccaatac catttggaat ggaattccat gtcagcgttg ggattctcag tatcctcaca      1140
agcatgacat gactcctgaa aatttcaagt gcaaggacct acgagaaaat tactgccgaa      1200
atccagatgg gtctgaatca ccctggtgtt ttaccactga tccaaacatc cgagttggtt      1260
actgctccca aattccaaac tgtgatatgt caaatggaca agattgttat cgtgggaatg      1320
gcaaaaatta tatgggcaac ttatcccaaa caagatctgg actaacgtgt tcaatgtgga      1380
acaagaacat ggaagactta caccgtcata tcttctggga accagatgca agtaagctga      1440
atgagaatta ctgccgaaat ccagatgatg atgctcatgg accctggtgc tacacgggaa      1500
atccactcat tccttgggat tattgcccta tttctcgttg tgaaggtgat accacaccta      1560
caatagtcaa tttagaccat cctgtaatat cttgcgccaa aacgaaacaa ctgcgagttg      1620
taaatgggat ccaacacga acaaatgtag gatggatgat tagtttgaga tacagaaata      1680
aacatatctg cggaggatca ttgataaagg aaagttgggt tcttactgca cgacagtgtt      1740
tcccttctcg agacttgaaa gattatgagg cttggcttgg aattcatgat gtccatggaa      1800
gaggagagga gaaacgcaaa caggttctca atgtttccca gctggtatat ggccctgaag      1860
gatcagatct ggttttaatg aagcttgcca gacctgctgt cctggatgat tttgttaata      1920
caattgattt acctaattat ggatgcacaa ttcctgaaaa gaccagttgc agtgtttatg      1980
gctgggcta cactggattg atcaactatg atggtctatt acgagtggca catctctata      2040
taatgggaaa tgagaaatgc agccagcatc accgagggaa ggtgactctg aatgagtctg      2100
aaatatgtgc tggggctgag aagattggat caggaccatg tgaggggat tatggtggcc       2160
cacttgtttg tgagcaacat aaaatgagaa tggttcttgg tgtcattgtt cccggccgtg      2220
gatgcgccat tccaaatcgt cctggtattt ttgtccgagt agcatattat gcaaaatgga      2280
```

```
tacacaaaat tattttaaca tataaggtac cacagtcata gctgaagtaa gtgtgtctga    2340
agcacccacc aatacaactg tcttttacat gaagatttca gagaatgtgg aattaaaaat    2400
accacttaca acaatcctaa gacaactact ggagagtcat gtttgttaaa attctcatta    2460
atgtttatgg gtgttttctg ttgttttgtt tgtcagtgtt attttgtcaa tgttgaagtg    2520
aattaaggta catgcaagtg tagtaacata tctcctgaag atacttgaat ggattaaaaa    2580
aacacacagg tataattgct ggataaagat tttgtgggga aaaaatcaat taatctctct    2640
aagctgcttt ctgaggttgg tttcttaata atgagtaaac cataaattaa atgttatttt    2700
aacctcacca aaacaattta taccttgtgt ccttaaattg taccctatat taaattatat    2760
tacatttcat atgctatatg ttatagttca ttcatttctc ttcaccatgt atcctgcaat    2820
actggtacac gaacacactt tttacaaaac cacataccca tgtacacatg cctaggtaca    2880
catgtacatg cactacagtt taaattatga tgtacttaat gtaacctcta aatatttag     2940 aagtatgtac ctatagtttt acctcaaaaa aatagaaatc tctaaagacc agtagaaata    3000
ttaaaaaatg atgcaaaatc aaaatgagtg gctaattctc catacgtaat ctgcagatga    3060
tcttctctgg ttgacatttt acgtgtggcc atcaccccgg gttaaataac acctaatcta    3120
ggtgtttaca tgtattcaat atcctagttt gtttcatgta gtttctaatt cttaaaggaa    3180
agagggtaat aattctattt gtgtaatttg tttcctccaa acttaaggcc acttatttac    3240
acaagatatt tgtatgtcta ctttcctaaa gcatttcttc agtgctcaga tcagtgtcta    3300
attgaagaag attaaaactg ctttggtcat taaaaacgta tttaaatagg ttaattctaa    3360
gacttgctgc tgtgattgac ttctagctca ctgcctttaa attttaaaaa atttaagagg    3420
aaaattttca tgtctccaaa gttttataaa taccctttcat caagtcatgc attaaagtat    3480
atattagaga aaaaaaaata cttttctcaa cctggaagat tttagcctaa taaagttttt    3540
ttgaagtaaa agaaaacttg taaagggaaa gaaactagtt tgtctaaaact ctgtattcat    3600 tttttttttt tttgaagtac agtggaatct gttgaatcag atattttatc aagatatctt    3660
tatttttcct tatttcattt ttacaaagat cactcccaat gccatatgta atagacattt    3720
aaatttcgtg ttctgtatga cagccaaatg atcatatttta tcattgtatt tgtcatgttt    3780
agctaaaaat catgtattgt tgagaaatag aataacaaaa agtaatagga taggctttga    3840 attttttgcaa aaaatcttcc tgtacaaaac atctttaaaa ataattttt gagtggtgtg    3900 aatctagtat tcccatttct ctgatttagt tttcttgagt gattttatc aaggctaagt     3960 ccccaaatga ttccctaaca gctctttaga ataccgttta atctggacta aaatggtttt    4020
aagtttatgg agagtttagt ccacagaact aactggactt ctggcggcaa gtccagaaat    4080
gcttatacaa attttttttt cataataaga tatgtgctgg tatcaaggaa cttaaagtgg    4140
aagcaaaaag acatccaagt agttgctagt ctccatcatc ttatctgatt gtatttctct    4200
tttccttata taatacacca ttttcataag aacacctaga aatttcaaga gtatattgcc    4260
aaaatataaa gtatatttcc tagtttcttc tggctgaacc agtgaaattt tattgttgca    4320
tattaatgat attttttaaa cttttataaa aattgtcata cttttaaata ctcacatttt    4380
aaaaatactt cttttatgac tcttcctcta aatttcctgg aaatacagat aaagattagc    4440
tagatacaag atgcagctaa gtatttagac attttgagcc cagtattttt cattttatta    4500
aaggctaaaa acaataccac caataaatca tcaaacaaac tgtacaaaat aattctgtct    4560
ttgggaggct ccttttgtga tagagggaca tgggtggaat tgacaatgaa agttagatga    4620
acaaggtccg tgttatttta ggtagtagaa cagggtagag tcatgtcatt atttgcgggc    4680
```

```
ggaagatact atttaccacg tgttctttgc tgaatcaatt attaaacatt tttaaaaatc    4740
caattatcca ctttattttg tgtcattgac aaaaggatct tttaagtcag aggttttcaat   4800 gtgattttg gcttggctgt ttgaataatg gttatgtact gttataattg tagacatttt     4860
ctcatgtcta ccaggaattg aagtgtaaaa ctaaaatatt tttcataatg cctctgccgt    4920
gcggaaggaa tgataatcct tttgtatact tctttaattt tattgtaaaa tgtgtaatga    4980
cttttaccta tatgctgtgg gcaggtcctc agtaaaatct attgagtcaa tttctagtat    5040
taataggctt ttgcttgcta tctaagtgtt tcaaattatg ggaagtgtga gacactggaa    5100
ggcaagaaaa ttaacaataa tggcatgtga tagcaaaatt gtatttcact tattcctgtg    5160
aatatttctt gttggtacca atggtactgt acaaagtgaa tgttatagcc acaacattct    5220
cttgaaaaga acactgtcaa gaagtgggaa attgctgtca ggcatttcgt tgttgttttt    5280
aaacttttta aaaagaaat actggttttg caagatagag atcatgaggt aaataatttt     5340
aataagctct tatactaaaa agccttaaat cgatttactg agattcaaaa catactatta    5400
taatcaatta tatcccatat atgtaggcaa actcatttaa aaaataaaat taattttggt    5460
aaaagtacat agtgtttgtt tttaaaatac ataattttaa aataaatcgc ttgtcatgat    5520
aaagtccaaa aagaagttat ctttcaatat tcaactaagt ttggagctaa gaatttacta    5580
atacaaaaaa aagttaaaat gttttggacc atatatatct tgacagtgta acttttaagt    5640
aggctcattt ccatttgcac agaaagtttc tgtctttagg aaactgaaaa tgaaatactg    5700
tggatgttat gactgtttgt cttctatgta aataggaaat taataagctg cctattgagt    5760
ggtatagctg tatgcttacc caaaaaggg aacactgtgg ttatgacttg tattataaac     5820
tttctgtagt taataaagtt gttatttttta taaccatgat tatatattat tattaataaa   5880
atattttatc gaaatgct                                                  5898

<210> SEQ ID NO 4
<211> LENGTH: 22
<212> TYPE: DNA
<213> ORGANISM: Artificial Sequence
<220> FEATURE:
<223> OTHER INFORMATION: Primer for hHGF

<400> SEQUENCE: 4
aaacgcaaac aggttctcaa tg                                             22

<210> SEQ ID NO 5
<211> LENGTH: 23
<212> TYPE: DNA
<213> ORGANISM: Artificial Sequence
<220> FEATURE:
<223> OTHER INFORMATION: Primer for hHGF

<400> SEQUENCE: 5
ctatgactgt ggtaccttat atg                                            23

<210> SEQ ID NO 6
<211> LENGTH: 21
<212> TYPE: DNA
<213> ORGANISM: Artificial Sequence
<220> FEATURE:
<223> OTHER INFORMATION: Primer for hHGF

<400> SEQUENCE: 6
cagcgttggg attctcagta t                                              21

<210> SEQ ID NO 7
```

```
<211> LENGTH: 21
<212> TYPE: DNA
<213> ORGANISM: Artificial Sequence
<220> FEATURE:
<223> OTHER INFORMATION: Primer for hHGF

<400> SEQUENCE: 7
cctatgtttg ttcgtgttgg a                                              21

<210> SEQ ID NO 8
<211> LENGTH: 23
<212> TYPE: DNA
<213> ORGANISM: Artificial Sequence
<220> FEATURE:
<223> OTHER INFORMATION: Primer for human [beta]-actin

<400> SEQUENCE: 8
cgtgacatca aagagaagct gtg                                            23

<210> SEQ ID NO 9
<211> LENGTH: 24
<212> TYPE: DNA
<213> ORGANISM: Artificial Sequence
<220> FEATURE:
<223> OTHER INFORMATION: Primer for human [beta]-actin

<400> SEQUENCE: 9
gctcaggagg agcaatgatc ttga                                           24
```

IMMUNE-COMPROMISED TRANSGENIC MICE EXPRESSING HUMAN HEPATOCYTE GROWTH FACTOR (HHGF)

CROSS-REFERENCE TO RELATED APPLICATIONS

This application is a National Stage of PCT/US2005/024788, filed Jul. 12. 2005, which claims priority to U.S. Provisional Application No. 60/1587,044 filed Jul. 13, 2004.

BACKGROUND INFORMATION

The signaling driven by hepatocyte growth factor/scatter factor (HGF/SF) and its receptor tyrosine kinase Met is an important target for therapeutic intervention. HGF/SF (also further abbreviated "HGF") is a multipotent growth factor that, through activation of its receptor Met, can induce many biological activities including proliferation, transformation, invasion and angiogenesis (Birchmeier et al. (2003) *Nat Rev Mol Cell Biol* 4: 915-925; Trusolino et al. (2002) *Nat Rev Canc* 4:289-300). Human and murine HGF are referred to herein as hHGF and mHGF, respectively. Human Met is also referred to as "hMet". Cells expressing Met are referred to herein as Met+ or hMet+ cells. Compelling evidence demonstrates that HGF/SF-Met signaling plays an important role in tumor development and, particularly, in the onset of invasion and metastatic process (Birchmeier et al., supra). Aberrant expression of Met and/or its ligand have been identified in almost all types of solid tumors derived from tissues of many different origins, and are correlated with poor prognosis. In addition, germline and/or somatic mutations of the Met receptor have been identified in several tumor types.

The growing list of agents with therapeutic potential targeting the HGF-Met pathway include:
(a) neutralizing antibody against human HGF/SF (Cao, B et al., *Proc. Natl. Acad. Sci.* 98:7443-7448:2001);
(b) NK4, an antagonist of HGF/SF (Date, K. et al., *Oncogene*17:3045-54, 1998);
(c) ribozymes targeting HGF and Met (Abounader, R et al., *FASEB J* 16:108-10, 2002);
(d) other small molecule drugs (Webb, C P et al., *Cancer Res* 60:342-49, 2000; Atabey, N et al., *J Biol Chem* 276:14308-14, 2001; Christensen, J G et al., Cancer Res. 63:7345-55 2003)

Immune-compromised "host" animals that support the growth of foreign cells and permit tissue xenografts have been used as preclinical models for testing drugs in addition to their utility for studying the biology of tumors in vivo (Mueller et al., 1991) *Cancer Metas Rev* 3:193-200; Kerbel (2003) *Cancer Biol Ther* 4 *Suppl.* 1: S134-39). However, the known animal "systems" are less than satisfactory because they are heterologous (or xenogeneic) to the tumors: implanted human tumor cells with human receptors are acted upon by mouse ligands (e.g., growth factors). These incompatibilities can lead to inappropriate selection of cells with a particular genotype that is manifest as an altered phenotype (compared to the same cell growing in a homologous environment). The importance of matching "donor" cells and tissues to the host is widely established in organ transplantation.

Growth of tissue xenografts in heterologous animal hosts can be significantly altered if, for example, the binding of host ligands with the donor cellular receptor are not of the appropriate high affinity. Thus far, most reagents targeting the HGF-Met pathway have been tested in athymic nude mice which can only provide the murine HGF ligand to the Met receptors of human tumor xenografts. Murine NIH3T3 cells can be transformed and become tumorigenic by ectopic expression of mouse Met but not of hMet (Rong, S et al., *Mol Cell Biol* 12:5152-58, 1992), which suggests that mouse HGF/SF might have low affinity for human Met receptors.

Transgenic (Tg) animals carry a gene which has been introduced into the germline of the animal, or an ancestor of the animal, at an early (usually one-cell) developmental stage. Many heterologous genes, including ones fused to murine or heterologous promoters, have been introduced into mice as transgenes. See, for example: Wagner, T. et al. (1981) *Proc Nat'l Acad. Sci USA* 78:5016; Stewart, T A et al. (1982) *Science* 217:1046; Constantini et al. (1981) *Nature* 294 92; Lacy et al. (1983) *Cell* 34:343; McKnight et al. (1983) *Cell* 34: 335; Brinster et al. (1983) *Nature* 306:332; Palmiter, R et al. (1982) *Nature* 300: 611; Palmiter et al. (1982) *Cell* 29: 701; Palmiter et al. (1983) *Science* 222:809; Leder, P. et al., U.S. Pat. No. 5,925,803; L. Hansson et al., U.S. Pat. No. 6,222,094

U.S. Pat. No. 6,107,540 (Sawyer, C L et al.), discloses an immune deficient mouse in which human prostate xenografts of locally advanced or metastatic prostate cancer are grown.

U.S. Pat. No. 5,643,551 (Namikawa, R. et al.,) discloses a method for initiating metastasis of human tumor cells under experimental conditions. Immunocompromised non-human mammals implanted with viable xenogeneic organ or tissue material are used as hosts for human tumor cells. The tumor cells are introduced into the chimeric animal after the solid tissue has been implanted and are then able to grow and metastasize as they would in situ. Therapeutic regimens may be evaluated in this system to determine efficacy against metastatic processes.

U.S. Pat. No. 5,530,179 (Terhorst C et al.), discloses a Tg mouse having a substantial deficiency in functionally active natural killer and T lymphocytes which is useful as a model system for immune diseases, tumorigenesis and transplant rejection.

U.S. Pat. No. 6,323,390 (Wu X-R et al.) discloses a Tg mouse containing an oncogene or a tumor suppressor gene operably linked to a urothelium-specific promoter in its germ cells and somatic cells as an animal model system for human bladder cancer.

U.S. Pat. No. 5,602,309 (Albers, K M et al.) discloses Tg mice that express increased levels of nerve growth factor (NGF) in the epidermis and other stratified, keratinized epithelium and that are useful in the study of neurodegenerative disorders of the brain such as Parkinson's disease and Alzheimer's disease and for testing for drug candidates for treating these diseases.

Ectopic in vivo expression of ligand transgenes in host animals can be used to influence the growth of xenografts (Bock, T A et al., *J Exp Med* 182:2037-43, 1995.). Investigators have described a Tg mouse model in which a murine HGF/SF transgene was ectopically overexpressed, leading to a dramatic increase liver size, enhanced liver regeneration and increased liver tumor formation (Sakata, H et al., *Cell Growth Differ* 7:1513-23, 1996).

There remains, however, a well-recognized need in the art for an animal model wherein the animals express a foreign, generally xenogeneic, ligand or growth factor which is genetically compatible with xenogeneic cells that are to be grown in that animal. The present inventors have accomplished this for one very important system, and describe herein ectopic expression of "hHGF" (a ligand) in a severe combined-immunodeficient (scid) mouse and the ability of this protein to enhance the growth of known human tumor cell lines that express Met, the receptor for hHGF.

SUMMARY OF THE INVENTION

The present invention is directed to a Tg vertebrate animal, preferably an immunocompromised non-human mammal, whose genome comprises a DNA sequence encoding hHGF or an active fragment or variant thereof, which is operably linked to an expression control sequence, wherein the expression of the hHGF in the mammal is effective in stimulating the growth of a human cells, preferably tumor cells or tissue which expresses an hMet receptor. The Tg mammal is a preferably a rodent, more preferably a mouse. Preferred immunocompromised mice include nude mice or most preferably, scid mice.

In the Tg mammal, the hHGF is preferably wild type hHGF, and the DNA sequence may encode an active fragment or variant of hHGF.

In the above Tg mammal, the expression control sequence preferably comprises a constitutive promoter which may be tissue specific; an inducible/repressible promoter or control element is also included. A preferred expression control sequence comprises a mouse metallothionein-1 (MT) promoter. Thus, a preferred Tg mammal is a homozygous scid mouse, preferably on the C3H background and expresses or the hHGF DNA wherein the coding sequence is operably linked to the mouse MT promoter.

The Tg mammal may be heterozygous or hemizygous for hHGF, or more preferably, homozygous for hHGF. It is preferably fertile.

Another embodiment comprises a Tg mammal as above which further comprises an implanted human, Met-expressing cell or tissue, preferably a human tumor cell. Preferred examples of human tumor cells are from the cell line SK-LMS-1, U118 or DU145.

In another embodiment, the Tg mammal comprises a human hepatocyte and/or human liver tissue.

In one embodiment of the above Tg mammal, the polynucleotide was introduced into the animal, or an ancestor thereof, at an embryonic stage.

Also provided is a cell, isolated from the Tg mammal, or a progeny cell of the isolated cell.

The invention includes a method for growing any Met+ cells in vivo in a non-human mammal, preferably a mouse, comprising introducing a Met+ cell or tissue, preferably a human cell or tissue, most preferably tumor cells or tissue but also human liver cells, into the above Tg mammal and permitting the cells to survive and/or grow. The tumor cells are preferably ones that grow into a solid tumor in the mammal, but may also be leukemia or lymphoma cells. In the Tg animal, the tumor cells may grow locally, migrate, circulate, extravasate, and metastasize in the mammal.

Also included is a method for testing an agent for its ability to inhibit the growth or metastasis of a Met+ human tumor, comprising exposing a Tg mammal of the invention to the test agent, before, concurrently with, or after implantation of Met+ tumor cells, and comparing the growth or metastasis of the tumor cells to a baseline value The baseline value is preferably the growth or metastasis of Met+ tumor cells which have been introduced into an optionally immunocompromised mammal that is not Tg for hHGF. The test agent may be an inhibitor of hMet and/or hHGF expression and/or activity, such as an inhibitor of Met-mediated tyrosine kinase activity.

The test agent in the above method may be a (1) small molecule or (2) a macromolecule such as an antibody, preferably a monoclonal antibody (mAb), that is preferably specific for hHGF or hMet, or (3) a nucleic acid which inhibits expression of hMet and/or hHGF Also provided is a method for evaluating the effect of a test agent or treatment as a potential therapy for a Met+ human tumor, comprising administering a test agent or treatment to a Tg mammal as above that comprises tumor cells, and comparing the growth or metastasis of the implanted tumor cell or tissue to a baseline value.

Another embodiment provides a method for producing an immunocompromised mouse which is Tg for hHGF, comprising incorporating into the genome of an immunocompromised mouse, at least one site, a polynucleotide encoding hHGF, or a biologically active fragment or variant thereof, which is operably linked to an expression control sequence, wherein the expression of the hHGF in the mouse is effective to support the growth or survival of Met+ human cells or tissue (preferably tumor or cancer cells or tissue).

The above method may further comprise backcrossing the Tg mouse with a scid/scid mouse for a sufficient number of generations to obtain a Tg mouse which is congenic for hHGF on the scid background, wherein expression of the polynucleotide in the Tg mouse is effective to support the growth of Met+ human tumor cells or tissue.

Also included is a method for preparing hHGF produced in a Tg non-human mammal, comprising collecting an hHGF-containing biological sample from the Tg mammal as above, preferably a mouse, wherein the sample may be serum or plasma, and the hHGF in the sample is optionally further enriched or purified.

BRIEF DESCRIPTION OF THE DRAWINGS

FIGS. 1A-1B are schematic representations of the process for breeding hHGF/SF Tg scid mice (also referred to as "hHGF Tg"). FIG. 1A describes the expression vector used. The hHGF/SF cDNA is under the control of the mouse metallothionein-1 (MT) gene promoter. FIG. 1B shows the breeding scheme used to generate congenic hHGF Tg scid mice. A hHGF Tg mouse was first generated on the C57BL/6 (B6) background, and then crossed with a C3H scid/scid mouse. The litters were PCR-genotyped for the hHGF transgene and mouse IgG was measured to determine the scid background. The $F_1$ generation hHGF Tg scid mice were then backcrossed to C3H scid/scid (shown as sc/sc) animals for ten generations to obtain doubly congenic hHGF/scid offspring.

FIG. 2A shows RT-PCR detection of hHGF transgene in mouse tissues. Total RNAs were prepared from different mouse tissues derived from scid control mice and hHGF Tg scid mice, respectively. RT-PCR was performed using the primer pair specific for hHGF. The arrow indicates the expression of hHGF. FIG. 2B shows the detection of hHGF protein in the Tg scid mice. Cell extracts were prepared from the control and hHGF Tg scid mouse livers, respectively. Immunoprecipitation was performed using anti-hHGF (A-7) mAb, followed by Western blot detection using anti-hHGF/SF (7-2) mAb. The arrow indicates the detected hHGF protein.

FIG. 4A shows RT-PCR analysis of hHGF. Total RNA was isolated from liver derived from normal B6, hHGF-Tg B6, control scid, and hHGF-Tg scid mice, respectively. RT-PCR was performed as described in Example I. The β-actin was used as an internal control. In each group, samples were obtained from three different animals. FIG. 4B shows the detection of hHGF protein by heparin beads pull-down assay. Liver homogenates (1 mg) prepared from each group mice were incubated with heparin-conjugated beads at 4° C. for 2 hr. Heparin-bound HGF was detected by anti-hHGF/SF antibody. Culture supernatant of the SK-LMS-1 cells stably transfected with hHGF (Jeffers, M et al. (1996) *Mol Cell Biol*.16: 1115-25) was used as a positive control (lane: SK).

FIG. 12A shows the relationship between age and liver weight. Liver weight was normalized by to body weight. Livers of hHGF-Tg C3H/scid mice were larger liver from the age of 3 weeks. FIG. 12B shows the relationship between body weight and liver weight. Only hHGF-Tg mice in the C3H/scid background had large livers (compared with other groups).

DESCRIPTION OF THE PREFERRED EMBODIMENTS

Figure 2B:
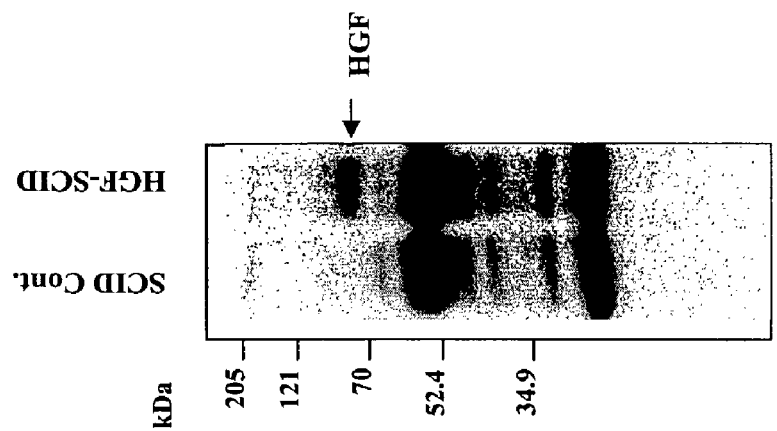
FIGS. 2A-2B show the detection of hHGF in Tg scid mice.

The present invention relates to an animal model for evaluating growth, survival and/or metastasis of xenotransplanted normal or tumor cells or tissue, in which a growth factor that stimulates cell growth in vivo is homologous to the xenotransplanted cells or tissue. That is, the animal comprises relevant biological molecules derived from the species from which the xenotransplanted material was derived. This results in enhanced growth of the transplanted cells. For example, the invention provides a Tg non-human vertebrate animal, preferably a mammal, preferably a rodent, such as a mouse, which is preferably immunocompromised, which animal provides a fertile environment for the growth of human cells. More specifically, the Tg animal produces a human growth factor in an amount effective to support the growth of cells, preferably tumor cells, that express receptors for the growth factor. In a most preferred embodiment, the genome of the animal comprises a polynucleotide which expresses the human growth factor, hHGF, Any Met-expressing human cells, preferably liver cells, can survive and grow in such animals. For disclosure of Met+ cells, see, for example, Birchmeier et al., 2003, supra. Also intended within the scope of the invention is the growth and propagation of HGF-dependent stem or progenitor cells of any lineage and at any stage of commitment or differentiation. HGF-dependent human cells of any type or class can be grown orthotopically in the animals of the present invention.

As shown in the Examples, the present inventors have bred a strain of Tg mice that express sequences encoding hHGF on the genetic background of an immunocompromised mouse carrying the "severe combined immunodeficiency" (scid) gene. Using these mice as recipients of human tumor xenografts, the present inventors have shown that the ectopically expressed hHGF ligand significantly enhances growth of human tumor cell lines that express the Met receptor, including, for example, the SK-LMS-1 human leiomyosarcoma cell line, U118 human glioblastoma cell line and DU145 human prostate cancer cell line and the DB-A2 subclone of the DBTRG-05MG glioblastoma multiforme cell line. By contrast, cells of the M14 human melanoma cell line, which has no detectable Met expression, did not benefit from any growth advantage in these novel mice. The presence of hHGF in these animals therefore specifically enhances Met-mediated cellular events in human tumor cells. Explanted human brain tumors that are HGF-dependent also grow successfully orthotopically in such mice.

Non-human Tg mammals of the invention are useful, highly sought-after tools to evaluate biological agents, including small molecule drugs, biotherapeutics and other therapeutic modalities that are directed to the disruption of HGF-Met signaling. The animals can be used, for example, for investigating HGF-Met signaling in vivo and for drug discovery or pre-clinical evaluation of candidate drugs or treatment regimens being developed to inhibit Met-mediated tumor growth and/or metastasis.

One aspect of the invention is a immunosuppressed or immunocompromised non-human Tg mammal (e.g., a rodent, preferably a mouse) whose genome comprises a DNA sequence encoding hHGF, or encoding a biologically active fragment or variant thereof, which is operably linked to an expression control sequence, wherein expression of the hHGF renders the animal more "permissive" for growth of an exogenously introduced Met+ human cell or tissue compared to an animal which does not express a hHGF transgene. The hHGF expressed in the non-human mammal effectively promotes, sustains or stimulates at least a detectable amount of growth of Met+ human tumor cells.

In general, the mammal of the present invention is genetically immunocompromised, either by virtue of an endogenous mutation or by introduction of a transgene (unrelated to HGF) that results in the immunocompromised phenotype. The animals need not be homozygous for the gene responsible for the immunodeficient trait, provided that appropriate backcrosses to a heterozygote for such a gene will generate an animal which has the immunocompromised phenotype and is homozygous for the hHGF transgene.

Suitable animals (that are immunocompromised where necessary) are available, or easily generated, using conventional methods, in a variety of genera, including rodents (e.g., rats), rabbits, guinea pigs, dogs, goats, sheep, cows, horses, pigs, llamas, camels or the like. In embodiments of the invention, the immunocompromised non-human mammal is scid or a nude mouse.

In preferred embodiments of the Tg animal, the polynucleotide encodes wild-type hHGF, or a biologically active fragment or variant of hHGF (e.g., one that stimulates Met). The expression control sequence may comprise a constitutive promoter or an inducible promoter, either of which may be tissue-specific. The mouse metallothionein-1 (MT) promoter is preferred. The mouse may be homozygous or heterozygous (hemizygous) for the hHGF. The animal may be a male or a female and is preferably fertile.

The immunocompromised mouse is preferably of a strain the genetic background of which is compatible with the promoter driving the expression of the hHGF nucleic acid. For the embodiments exemplified herein, a mouse of the C3H background is preferred. It is within the skill of the art to assess without undue experimentation whether a given promoter (and optionally, additional expression control sequences) drives adequate expression of hHGF in a given inbred mouse strain. Similarly, it is possible to test whether an immunocompromised mouse which is heterozygous (i.e., hemizygous) for hHGF makes adequate amounts of hHGF to promote growth of Met+ cells.

In a most preferred embodiment, the Tg animal is a scid mouse homozygous for a polynucleotide encoding hHGF, operably linked to an MT promoter.

In other embodiments of this invention, the Tg animal further comprises an implanted human, Met+ tumor cell or non-tumor tissue, non-limiting examples of which are the cell lines SK-LMS-1, U118 or DU145, DB-A2 and human hepatocytes or liver tissue fragments. The polynucleotide encoding hHGF in the Tg mouse was either introduced into the subject animal, or more preferably, into an ancestor thereof, at an embryonic stage.

The invention includes a Met-expressing cell isolated from a Tg animal as described above, or progeny of such a cell. In the case of tumor cells, for example, growth of the cells in the above animal will be expected to select for cells expressing higher levels of Met. Thus, stable human tumor cells or cell lines expressing higher levels of Met may be obtained in this way and stored frozen or passaged continuously in such animals.

Example VI shows markedly enlarged livers, and enhanced liver regeneration rate after partial hepatectomy, in C3H hHGF Tg scid mice. Thus, such animals can be used to grow human hepatocytes and/or functional human liver tissue, which may subsequently implanted back into humans (transiently or long-term) for the treatment any of a number of diseases associated with liver insufficiency.

Another aspect of the invention is a method for growing hMet+ tumor cells in vivo in a non-human animal as above. The method comprises introducing hMet+ tumor cells or tissue into a Tg animal of the invention (e.g., a mouse) which tumor cells or tissue grow to form a tumor and/or the cells migrate and the tumor metastasizes in the animal.

Other aspects of the invention relate to testing methods, one embodiment of which is a method for testing a candidate agent, e.g., a small organic molecule or biological agent, for its ability to inhibit the growth or metastasis of an hMet+ human tumor. The method comprises exposing a non-human Tg mammal of the invention (e.g., a rodent, preferably a mouse) to the candidate agent, before, concurrently with, or after introducing hMet+ tumor cells or tissue into the animal, and comparing cell growth and/or metastasis compared to a baseline value. As used herein, a "baseline value" may include (a) the amount of growth or metastasis of hMet+ tumor cells which have been introduced into a mammal (e.g., an immunocompromised mammal) of the invention that is not transgenic for hHGF; (b) growth or metastasis of hMet+ tumor cells which have been introduced into other types of control animals; or (c) a database with data compiled from a study or studies that produce any of such experimental values.

The agent may be an inhibitor of hMet and/or hHGF expression or activity. This may include an agent that inhibits (1) binding of hHGF to Met, (2) induction of Met-mediated kinase activity, (3) hHGF's ability to influence a post-binding event in the hHGF/Met signalling pathway and/or (4) hHGF's ability to stimulates tumor growth or metastasis. The agent may be a small molecule or a macromolecule, such as an antibody (preferably specific for hMet, hHGF).

Another such agent is a nucleic acid that inhibits expression of hMet and/or hHGF (such as RNAi, antisense oligonucleotides or ribozymes). The agent being tested may also be a "physical agent" such as any appropriate form and dose of irradiation (such as ionizing radiation) or an anti-Met antibody or combination of antibodies (e.g., mAbs)

Prior to, or in conjunction with, such therapy, radioscintigraphic agents based on anti-Met antibodies, for example, may be used to localize the Met+ tumor cells, including metastases or micrometastases, in these animals. See, for example, Hay et al., WO 03/057155, based on commonly assigned patent application PCT/US02/41607, which is hereby incorporated by reference in its entirety. Such localization would then guide locally- or regionally-targeted therapeutic efforts.

Also provided is a method for evaluating the effect of a test therapy for a hMet+ human tumor (which includes a tumor of which at least some cells are Met+). This method comprises introducing into a Tg mammal as above hMet+ tumor cells or tissue and before, during or after introducing those cells, treating the mammal with the test therapy, and comparing the growth and/or metastasis of the hMet+ tumor cells or tissue to a baseline value. The potential therapy may involve ionizing radiation, photodynamic therapy, gene therapy, etc.

The Tg mammal used in any of the testing methods of the invention may take any of the forms described herein.

Also provided is a method for producing a Tg immunocompromised non-human mammal, preferably a rodent, such as a mouse, comprising incorporating into the genome of an immunocompromised non-human mammal (preferably a scid/scid mouse) at least one allele that comprises a copy of a polynucleotide encoding hHGF, or an active fragment or variant thereof, the coding polynucleotide being operably linked to an expression control sequence, wherein the expression of the hHGF in the mammal is effective to support the growth of a human tumor cell or tissue which expresses an hMet receptor. In another embodiment, this method further comprises backcrossing the Tg mammal produced as above with a mammal having the immunosuppressed genotype of the parent (e.g., a scid/scid mouse) for a sufficient number of generations to obtain a Tg mammal which is congenic for hHGF on the immunosuppressed (e.g., scid) background, wherein expression of the polynucleotide in the Tg mammal is effective to support the growth of a human tumor cell or tissue which expresses an hMet receptor. Animals, such as mice, wherein the hHGF is on a congenic or isogenic background is preferred for reproducibility and uniformity of results. Generally, about 10 such crosses are sufficient to generate the desired genotype. As noted above, the strain background should be compatible with the selected promoter and/or expression control sequences that drive hHGF expression; a mouse of a C3H strain (without limitation as to substrains) is a preferred mouse strain for the embodiments exemplified herein.

Another aspect of the invention is a method for producing hHGF, comprising collecting hHGF from a Tg animal of the invention that is expressing hHGF. The hHGF may be collected from any suitable source in the animal, including a biological fluid or cells that secrete the hHGF polypeptide.

The invention relates to a Tg, immunocompromised, non-human mammal, whose genome comprises, for example, DNA encoding hHGF.

A sequence encoding an HGF, or an active fragment or variant thereof, is sometimes referred to herein as a "transgene."

The animal from which the progeny animal is descended is referred to as "progenitor animal." "Progeny" of a progenitor mammal any animals which are descended from the progenitor as a result of sexual reproduction or cloning of the progenitor, and which have inherited genetic material from the progenitor. In this context, cloning refers to production of genetically identical offspring from DNA or a cell(s) of the progenitor animal. As used herein, "development of an animal" from a cell or cells (embryonic cells, for example), or development of a cell or cells into an animal, refers to the developmental process that includes growth, division and differentiation of a fertilized egg or embryonic cells (and their progeny) to form an embryo, and birth and development of that embryonic animal into an adult animal.

An animal is "derived from" a Tg ovum, sperm cell, embryo or other cell if the Tg ovum, sperm cell, embryo or other cell contributes DNA to the animal's genomic DNA. For example, Tg embryo of the invention can develop into a Tg animal of the invention. A Tg ovum of the invention can be fertilized to create a Tg embryo of the invention that develops into a Tg animal of the invention. A Tg sperm of the invention can be used to fertilize an ovum to create a Tg embryo of the invention that develops into a Tg animal of the invention. A Tg cell of the invention can be used to clone a Tg animal of the invention.

As used herein, a "transgenic ('Tg') non-human mammal" is a mammal into which an exogenous recombinant construct has been introduced, or its progeny. Such a mammal may have developed from (a) embryonic cells into which the construct has been directly introduced or (b) progeny cells of (a). As used herein, an "exogenous construct" is a nucleic acid that is artificially introduced, or was originally artificially introduced, into an animal. The term "artificial introduction" excludes introduction of a construct into an animal through normal reproductive processes (such as by cross breeding). However, animals that have been produced by transfer of an exogenous construct through the breeding of a mammal comprising the construct (into whom the construct was originally "artificially introduced") are considered to "comprise the exogenous construct." Such animals are progeny of animals into which the exogenous construct has been introduced.

A non-human Tg mammal of the invention is preferably one whose somatic and germ cells comprise at least one genomically integrated copy of a recombinant construct of the invention (a recombinant construct comprising a sequence encoding HGF (preferably hHGF), or an active fragment or variant thereof, which sequence is operably linked to an expression control sequence. Alternatively, the disclosed transgene construct can also be assembled as an artificial chromosome, which does not integrate into the genome but which is maintained and inherited substantially stably in the animal. Artificial chromosomes of more that 200 kb can be used for this purpose.

The invention further provides a Tg gamete, including an Tg ovum or sperm cell, a Tg embryo, and any other type of Tg cell or cluster of cells, whether haploid, diploid, or of higher zygosity having at least one genomically integrated copy of a recombinant construct of the invention. The Tg gamete, ovum, sperm cell, embryo, somatic cell or animal cell, may comprise two or more copies of the transgene. These are preferably tandemly arranged or may be inserted at noncontiguous sites in the haplotype (and genome)

As used herein, the term "embryo" includes a fertilized ovum or egg (i.e., a zygote) as well as later multicellular developmental stages of the organism. The recombinant construct is preferably integrated into the animal's somatic and germ cells, or is present in stable extrachromosomal form, such as an artificial chromosome, that is stable and heritable. The Tg animal or cell preferably contains a multiplicity of genomically integrated copies of the construct. Preferably, multiple copies of the construct are integrated into the host's genome in a contiguous, head-to-tail orientation.

Also included herein are progeny of the Tg animal that preferably comprise at least one genomically integrated copy of the construct, and Tg animals derived from a Tg ovum, sperm, embryo or other cell of the invention.

In some embodiments of the invention, the Tg animal is sterile although, preferably, it is fertile. The present invention further includes a cell line derived from a Tg embryo or other Tg cell of the invention, which contains at least one copy of a recombinant construct of the invention. Methods of isolating such cells and propagating them are conventional.

The non-human Tg mammal of the invention is preferably immunocompromised. Preferably this state is achieved by a mutation that the animal carries which renders it less capable or incapable of immunologically rejecting foreign, preferably xenogeneic, most preferably human tumor cells. In one embodiment of the invention, the mammal is homozygous for the nude mutation (nu/nu). In a preferred embodiment, the mammal is a mouse homozygous for the scid mutation.

While the mouse is preferred, the present invention includes other genera and species, such as other rodents (e.g., rats), rabbits, guinea pigs, dogs, goats, sheep, cows, pigs, llamas, camels, etc.

The success rate for producing Tg animals by microinjection is highest in mice, where approximately 25% of injected fertilized mouse ova which have been implanted in an appropriately prepared female, will develop into Tg mice. Success rates with rabbits, pigs, sheep and cattle are lower (Jaenisch, R.(1988) *Science* 240,1468-1474; Hammer et al. (1985) *Nature* 315, 680; and Wagner et al. (1984) *Theriogenology* 21,29).

Methods of producing Tg animals are well within the skill of those in the art. The hHGF Tg animal of the invention is preferably produced by introducing the construct/transgene into the germline, by introduction into an embryonic target cell at any of several developmental stages. Different methods are used depending on the stage of development. The zygote is the preferred target for microinjection.

The introduction of a construct of the invention such as a DNA molecule comprising a transgene sequence, preferably encoding hHGF, at the fertilized oocyte stage ensures the presence of the introduced gene in all of the germ cells and somatic cells of the Tg animal.

Presence of the transgene in the germ cells of the Tg "founder" animal means that all of its offspring will carry that gene in all of their germ and somatic cells. If a sequence is introduced at a later embryonic stage, it may be absent from a proportion of the founder's somatic cells. Nevertheless, the founder's offspring that inherit the introduced sequence will carry it in all of their germ and somatic cells.

Any method known in the art for introducing a recombinant construct (transgene) into an embryo, such as microinjection, gene gun, transfection, liposome fusion, electroporation, and the like, may be used to produce Tg animals. The most widely used and preferred method is microinjection. A DNA molecule is injected into the male pronucleus of fertilized eggs (Brinster et al. (1981) *Cell* 27, 223; Costantini et al. (1981) *Nature* 294, 92; Harbers et al. (1981) *Nature* 315, 680; Wagner et al. (1981) *Proc. Natl. Acad. Sci. USA* 78, 5016; U.S. Pat. Nos. 4,873,191 and 6,872,868 to T. Wagner et al.; Gordon et al. (1976) *Proc. Natl. Acad. Sci. USA* 73, 1260; Stewart et al. (1982) *Science* 217,1046-1048; Palmiter et al. (1983) *Science* 222, 809; Brinster et al. (1985) *Proc. Natl. Acad. Sci. USA* 82, 4438-4442 (1985); Hogan et al. (1986) *Manipulating the Mouse Embryo: A Laboratory Manual*, Cold Spring Harbor Laboratory; U.S. Pat. Nos. 4,870,009; 5,550,316; 4,736,866; 4,873,191). DNA may also be microinjected into the cytoplasm of a zygote.

The above methods for introducing a recombinant construct/transgene into mammals and their germ cells were originally developed in the mouse and subsequently adapted to larger animals, including livestock species (WO 88/00239, WO 90/05188, WO 92/11757; and Simon et al. (1988) *Bio/Technology* 6,179-183).

The transgene can also be introduced by retroviral infection A developing mammalian embryo can be cultured in vitro to the blastocyst stage. During this time, the blastomeres, preferably after enzymatic treatment to remove the zona pellucida, are used as targets for retroviral infection (Jaenisch (1976) *Proc. Natl. Acad. Sci. USA* 73, 1260-1264).

A typical viral vector system for introducing the transgene is a replication-defective retrovirus (Jahner et al. 1985) *Proc. Natl. Acad. Sci. USA* 82, 6927-6931; Van der Putten et al. (1985) *Proc. Natl. Acad. Sci. USA* 82, 6148-6152). Transfection is carried out by culturing the blastomeres on a monolayer of virus-producing cells (Van der Putten et al., supra; Stewart et al. (1987) *EMBO J.* 6, 383-388). Infection can also be performed at a later stage. The transgene may be introduced into the germ line by intrauterine retroviral infection of the midgestation embryo (Jahner et al., supra). Virus or virus-producing cells can be injected into the blastocoel (Jahner et al. (1982) *Nature* 298, 623-628).

Most founders produced as above will be mosaic for the transgene since it is incorporated in a subset of the cells which formed the Tg animal. Further, the transgene may have inserted in various positions in the genome which generally will segregate in the offspring.

Another type of target cell into which the transgene may be introduced is the embryonic stem (ES) cell. ES cells are obtained from pre-implantation embryos cultured in vitro and are fused with embryos (Evans et al. (1981) *Nature* 292, 154-156; Bradley et al. (1984) *Nature* 309, 255-258; Gossler et al. (1986) *Proc. Natl. Acad. Sci. USA* 83, 9065-9069; Robertson et al. (1986) *Nature* 322, 445-448). Transgenes can be efficiently introduced into ES cells by direct DNA transfection or by retrovirus-mediated transduction. The transformed ES cells can thereafter be combined with blastocysts from a mammal. The ES cells colonize the embryo and contribute to the germ line of the resulting chimeric animal. For a review see Jaenisch, R. (1988) *Science* 240, 1468-1474; Sedivy et al. *Gene Targeting*, W. H. Freeman and Company, N.Y., 1992, pp. 123-142.

Procedures for embryo manipulation and microinjection are described in, for example, Hogan et al., eds., *Manipulating the Mouse Embryo*, Cold Spring Harbor Laboratory Press, Cold Spring Harbor, N.Y., 1986.

In an exemplary embodiment, mouse zygotes are collected from 6 week old "primed" females that have been superovulated with pregnant mares serum (PMS) followed 48 hours later with human chorionic gonadotropin (hCG). The PMS induces follicular growth and hCG induces ovulation. Primed females are placed with fertile males and checked for vaginal plugs on the following morning as a sign of mating. Zygotes are collected from these females after mating and cumulus cells are removed. Pronuclear embryos are recovered. Embryos are recovered in a Dulbecco's modified phosphate buffered saline (DPBS) and maintained in Dulbecco's modified minimal essential medium (DMEM) supplemented with 10% fetal bovine serum.

Tg animals can be identified after birth by standard protocols. For instance, at three weeks of age, a short tail sample is excised for DNA analysis. The tail sample is digested by incubating overnight at 55° C. in the presence of a buffer such as 0.7 ml 50 mM Tris, pH 8.0, 100 mM EDTA, 0.5% SDS and about 350 mg of proteinase K. The digested material is extracted once with equal volume of phenol and once with equal volume of phenol:chloroform (1:1). The supernatants are mixed with 70 ml 3M sodium acetate (pH 6.0) and the nucleic acid precipitated by adding an equal volume of 100% ethanol. The precipitate is collected by centrifugation, washed once with 70% ethanol, dried and dissolved in 100 ml TE buffer (10 mM Tris, pH 8.0 and 1 mM EDTA). The DNA is then cut with BamHI and BglII or EcoRI (or other frequent DNA cutter), electrophoresed on 1% agarose gels, blotted onto nitrocellulose paper and hybridized with labeled primers under very stringent conditions in order to discern between murine hHGF and hHGF genes. Alternatively, a ligation chain reaction (LCR) (Landegran et al. (1988) *Science* 241, 1077-1080; Nakazawa et al. (1994) *Proc. Natl. Acad. Sci. USA* 91, 360-364), which is useful for detecting point mutations, can be used to determine the presence of the transgene in the neonate. Alternatively, PCR amplification of genomic DNA isolated from the tail tissue is performed, as described in Example I herein.

The resulting Tg mice or founders are bred and the offspring analyzed to establish lines from the founders that express the transgene. In the Tg animals, multiple tissues can be screened to observe expression, for example, by Northern blots, to evaluate independence of integration site and expression levels. By crossbreeding and inbreeding the Tg non-human animals according to the present invention, as well known in the art, the offspring may be heterozygous (hemizygous) or homozygous for the hHGF and heterozygous or homozygous for the gene responsible for the immunocompromised phenotype. A typical mating scheme for generating mice congenic for hHGF on the genetic background of C3H scid animals is shown in FIG. 1B. These and other methods for producing Tg animals in a variety of species are now conventional and well-known to those skilled in the art.

The present invention is also directed to the creation of immune-compromised Tg mice in whom tissue specific expression of the hHGF transgene is driven by a tissue specific promoter, as is discussed more extensively below.

Also included in the present invention is a hHGF knock-in mouse in which the native murine HGF/SF gene is replaced with its human counterpart using gene-targeting technology. Procedures for generating such knock-in mice are conventional.

The tissue-specific hHGF Tg mice can be a powerful tool for the study of orthotopic tumor formation and metastasis of human tumor cells derived from particular organ or tissue type, such as liver, prostate, mammary gland, etc. The advantage of hHGF knock-in mice is that the animal expresses the hHGF protein in the same temporal and spatial fashion as normal mice express murine HGF/SF, and do so in an otherwise normal body. Thus, such mice provide only the species-compatible hHGF ligand for a given human tumor xenograft under test, thereby supplanting rather than supplementing murine HGF/SF). Such animals are particularly useful for transplantation of primary or metastatic human tumors from patients to determine their drug sensitivity patterns.

As used herein, the term "polynucleotide" is interchangeable with "oligonucleotide" and "nucleic acid." A polynucleotide of the present invention may be recombinant, natural, or synthetic or semi-synthetic, or any combination thereof. Polynucleotides of the invention may be RNA, PNA, LNA, or DNA, or combinations thereof. As used herein, the terms peptide, polypeptide and protein are also interchangeable.

A "recombinant construct" (also referred to herein as a "construct" for short) or a "transgene" which is used to generate a Tg animal of the invention is a polynucleotide which comprises a sequence encoding an HGF (preferably hHGF), or an active fragment or variant thereof, which is operably linked to an expression control sequence. The coding sequence comprises hHGF exon sequences, although it may optionally include intron sequences which are either derived from a hHGF genomic DNA or DNA of an unrelated chromosomal gene. An exemplary recombinant construct comprises a hHGF cDNA sequence, SEQ ID NO: 3, shown in Example I.

A construct of the invention may comprise an "active fragment" or an "active variant" of a sequences encoding HGF, e.g., hHGF. Such an active fragment or variant encodes a form of HGF that exhibits at least a measurable degree of at least one biological activity of HGF. For example, a polypeptide encoded by an "active" fragment or variant can, through activation of the Met receptor, induce a biological response such as proliferation (e.g., stimulation of the growth of human Met-expressing tumor cells), tumorigenic transformation, invasion, evasion of apoptosis (i.e., increased survival) and/or angiogenesis, or it can competitively inhibit the binding of a native hHGF polypeptide to a Met receptor. A skilled worker can readily test whether a polynucleotide of interest exhibits this desired function, by employing well-known assays, such as those described elsewhere herein.

An active fragment of the invention may be of any size that is compatible with, for example, the requirement that it encode a polypeptide that can stimulate the growth of human Met-expressing tumor cells. For example, an HGF-encoding sequence can be shortened by about 20, about 40, or about 60nucleotides, etc.) provided that the polynucleotide retains the desired activity.

An active variant of the invention includes, for example, polynucleotides comprising a sequence that exhibit a sequence identity to DNA encoding wild type hHGF, e.g., SEQ ID NO:3, of at least about 70%, preferably at least about 80%, more preferably at least about 90% or 95%, or 98%, provided that the polynucleotide encodes a polypeptide with the desired activity. In accordance with the present invention, a sequence being evaluated (the "Compared Sequence") has a certain "percent identity withh," or is a certain "percent identical to" a claimed or described sequence (the "Reference Sequence") after alignment of the two sequences. The "Percent Identity" is determined according to the following formula:

$$\text{Percent Identity}=100[1-(C/R)]$$

In this formula, C is the number of differences between the Reference Sequence and the Compared Sequence over the length of alignment between the two sequences wherein (i) each base in the Reference Sequence that does not have a corresponding aligned base in the Compared Sequence, and (ii) each gap in the Reference Sequence, and (iii) each aligned base in the Reference Sequence that is different from an aligned base in the Compared Sequence constitutes a difference. R is the number of bases of the Reference Sequence over the length of the alignment with the Compared Sequence with any gap created in the Reference Sequence also being counted as a base.

If an alignment exists between the Compared Sequence and the Reference Sequence for which the Percent Identity (calculated as above) is about equal to, or greater than, a specified minimum, the Compared Sequence has that specified minimum Percent Identity even if alignments may exist elsewhere in the sequence that show a lower Percent Identity than that specified.

In a preferred embodiment, the length of aligned sequence for comparison purposes is at least 30%, preferably at least 40%, more preferably at least 50%, even more preferably at least 60%, and even more preferably at least 70%, 80%, or 90% of the length of the Reference Sequence.

The comparison of sequences and determination of percent identity (and percent similarity) between two sequences can be accomplished using any of a number of mathematical algorithms. See, for example, Lesk, A M, ed., *Computational Molecular Biology*, Lesk, Oxford University Press, New York, 1988; Smith, D W, ed., *Biocomputing: Informatics and Genome Projects*, Academic Press, New York, 1993; Griffin, A M et al., eds., *Computer Analysis of Sequence Data, Part 1*, Humana Press, New Jersey, 1994; von Heinje, G., *Sequence Analysis in Molecular Biology*, Academic Press, 1987; and Gribskov, M et al., eds., *Sequence Analysis Primer*, Stockton Press, New York, 1991.

A preferred example of such an algorithm is described in Karlin et al. (1993) *Proc. Natl. Acad. Sci. USA* 90, 5873-5877, and is incorporated into the NBLAST and XBLAST programs (version 2.0) as described in Altschul et al. (1997) *Nucleic Acids Res.* 25, 3389-3402. When utilizing BLAST and Gapped BLAST programs, the default parameters of the respective programs (e.g., NBLASST) can be used. In one embodiment, parameters for sequence comparison can be set at score=100, wordlength (W)=12, or can be varied (e.g., W=5 or W=20).

In a preferred embodiment, the percent identity between two nucleotide sequences is determined using the GAP program in the GCG software package (Devereux et al. (1984) *Nucleic Acids Res.* 12 (1):387) using a NWSgapdna. CMP matrix and a gap weight of 40, 50, 60, 70, or 80 and a length weight of 1,2,3,4,5 or 6.

Another algorithm utilized for the comparison of sequences is that of Myers and Miller, CABIOS (1989), and is incorporated into the ALIGN program (version 2.0; part of the CGC software package (supra). Additional known algorithms for sequence analysis include ADVANCE and ADAM (Torellis et al. (1994) *Comput. Appl. Biosci.* 10, 3-5); and FASTA Pearson et al. (1988) *Proc. Nat'l. Acad. Sci.* 85, 2444-2448).

The term "substantially homologous" as used herein means that two nucleotide sequences are at least about 90%-100% identical. A substantially homologous sequence of the invention can hybridize to one of the nucleic acid sequences mentioned above, or to a portion thereof, under conditions of high stringency. Hybridization at "high stringency" is a term well recognized in the art. Conditions of "high stringency" are well known, and, according to this invention, are achieved for example by incubating a blot overnight (e.g., at least 12 hours) with a long polynucleotide probe in a hybridization solution containing, about 5× SSC, 0.5% SDS, 100 µg/ml denatured salmon sperm DNA and 50% formamide, at 42° C. Blots can be washed at high stringency conditions that allow, e.g., for less than 5% bp mismatch, by washing twice in 0.1× SSC and 0.1% SDS for 30 min at 65° C., thereby selecting sequences having, 95% or greater sequence identity. Other non-limiting examples of high stringency conditions include a final wash at 65° C. in aqueous buffer containing 30 mM NaCl and 0.5% SDS. Another nonlimiting example of high stringent conditions is hybridization in 7% SDS, 0.5 M NaPO$_4$, pH 7, 1 mM EDTA at 50° C. overnight, followed by one or more washes with a 1% SDS solution at 42° C.

Whereas high stringency washes can allow for less than 5% mismatch, reduced or low stringency conditions can permit up to 20% nucleotide mismatch. Hybridization at low stringency can be accomplished as above, but using lower formamide conditions, lower temperatures and/or lower salt concentrations, as well as longer periods of incubation time. Again, this is conventional in the art.

An active variant of the invention may take any of a variety of forms, including, e.g., a naturally or non-naturally occurring polymorphisms, including single nucleotide polymorphisms (SNPs), allelic variants, and mutants. The variant may comprise one or more additions, insertions, deletions, substitutions, transitions, transversions, inversions, or chromosomal translocations or the like; the variant may result from an alternative splicing event. Any combination of the foregoing is also intended. Other types of active variants will be evident to one of skill in the art. For example, the nucleotides of a polynucleotide can be joined by known linkages, e.g., ester, sulfamate, sulfamide, phosphorothioate, phosphoramidate, methylphosphonate, carbamate, etc., depending on the desired purpose, such as improved in vivo stability, etc. See, e.g., U.S. Pat. No. 5,378,825. Any desired nucleotide or nucleotide analog such as 6-mercaptoguanine, 8-oxoguanine, etc. can be incorporated.

Active variants or fragments of the invention also includes polynucleotides which encode HGF polypeptides that differ from wild type hHGF, yet retain at least one of the hHGF functions noted above. For example, the polypeptide may comprise a sequence that differs from the wild type hHGF sequence by one or more conservative amino acid substitutions, or that is at least about 70% identical, preferably at least about 80%, 90%, 95% or 98% identical, to the wild type sequence. The wild type sequence of hHGF is encoded by the cDNA having the sequence SEQ ID NO: 3.

In the present recombinant construct, a hHGF coding sequence, or active fragment or variant thereof, is operably linked to an "expression control sequence", which term means a polynucleotide sequence that regulates expression of a polypeptide from the coding sequence to which it is functionally ("operably") linked. Expression can be regulated at the level of transcription or translation. Thus, an expression control sequence may include transcriptional elements and translational elements. Such elements include promoters, domains within promoters, upstream elements, enhancers, elements that confer tissue- or cell-specificity, response elements, ribosome binding sequences, transcriptional terminators, etc. A expression control sequence is operably linked to a nucleotide coding sequence when it is positioned in such a manner to drive or control expression of the coding sequence. For example, a promoter operably linked 5' to a coding sequence drives expression of the coding sequence. One expression control sequence may be linked to another expression control sequence. For example, a tissue-specific expression control sequence may be linked to a basal promoter element.

Any of a variety of expression control sequences can be used in constructs of the invention. In preferred embodiments, the expression control sequence comprises a constitutive promoter, which is expressed in a wide variety of cell types. Many such suitable expression control sequences are well-known in the art. Among the suitable strong constitutive promoters and/or enhancers are expression control sequences from DNA viruses (e.g., SV40, polyoma virus, adenoviruses, adeno-associated virus, pox viruses, CMV, HSV, etc.) or from retroviral LTRs. Tissue-specific promoters well-known in the art maybe be used to direct expression of hHGF to specific cell lineages.

While the experiments discussed in the Examples below were conducted using the mouse MT gene promoter, other MT-related promoters capable of directing MT gene expression can be used to yield similar results as will be evident to those of skill in the art. An example is shorter MT 5'-upstream sequences, which can nevertheless achieve the same degree of expression. Also useful are minor DNA sequence variants of the MT promoter, such as point mutations, partial deletions or chemical modifications.

The MT promoter is known to be expressible in rats, rabbits and humans, and may be expressed in any other mammalian species, a fact which may be determined by routine testing. In addition, sequences that are similar to the 5' flanking sequence of the mouse MT gene, including, but not limited to, promoters of MT homologues of other species (such as human, cattle, sheep, goat, rabbit and rat), can also be used. The MT gene is sufficiently conserved among different mammalian species that similar results with other MT promoters are expected.

For tissue-specific expression of the transgene in the Tg animal, the coding sequence must be operably linked to an expression control sequence that drives expression specifically in that tissue. Suitable tissue-specific expression control sequences include the following: MMTV-LTR (for mammary-specific expression), etc.

Inducible/Repressible Expression Control Systems

An inducible promoter is one which, in response to the presence of an inducer, is activated. Hence, a coding sequence driven by an inducible promoter can be turned on or off by providing or withdrawing the inducer. A promoter may be homologous, derived from the same species as the coding sequence. Preferably, the promoter is heterologous, that is, derived from another species, or even from a virus. hHGF constructs in accordance with the present invention may be operably linked to an inducible or repressible control elements. An repressible system, described by Gossen, M. et al., *Proc Natl Acad Sci USA* 89:5547-51 (1992), is based on the use of control elements of the tetracycline-resistance operon encoded in Tn10 of *E. coli*. The tet repressor is fused with the activating domain of Herpes simplex virus VP16 to generate a tetracycline-controlled transactivator. Such a transactivator is used to stimulate transcription from a promoter sequence, such as the CMV promoter IE.

A gene controlled by a promoter acting under the influence of the tetracycline-controlled transactivator can be constitutively expressed and turned off by using an effective concentration of tetracycline. Such a system can regulate a gene over about five orders of magnitude. The tetracycline-repressible system functions in vivo in mice, where tetracycline administration via the diet is used to keep the expression of the inducible gene off. Tetracycline analogs which cross the blood-brain barrier can be used if gene activity is desired in the brain.

Two steps of transfection may be used to produce the appropriate system. A first transfection is used to isolate clones expressing the transactivator. The best clones are identified by testing each in a transient transfection assay for the ability to express a marker gene, such as an estrogen-dependent luciferase. The second transfection involves the hHGF coding sequence under control of an inducible promoter into a transactivator-containing clone. One strategy involves first isolating a stable cell line expressing the inducible hHGF protein or peptide by cotransfection of both plasmids into appropriate target cells. After selection, for example with G418, clones showing estrogen-dependent expression of hHGF may be detected by an immunoassay or biological assay. To increase the rate of plasmid integration and to stabilize the integrated plasmids in the host genome, the plasmids are preferably linearized and cotransfected into cells in the presence of mammalian high molecular weight DNA as a carrier.

The relative advantages of a two vector system, as described above, over a single vector system involving a larger plasmid is that in a two vector system, multiple copies of the reporter plasmid (encoding the gene of interest) may be needed to obtain a detectable biological effect in a cell, while one or only a few copies of the transactivator-carrying plasmid may suffice.

According to the present invention, the hHGF DNA molecule is placed under the control of a promoter subject to regulation by a tetracycline-controlled transactivator. Such a construct (in a single vector or preferably two vector form) is delivered into target cells, whether embryonic, adult normal or tumor, either in vitro or in vivo. To express the hHGF, tetracycline is withheld so that the hHGF DNA is expressed. To prevent the action of the hHGF, for example, locally, tetracycline or an active congener of tetracycline is administered locally to the cells transfected with the constructs. Effective systemic doses (oral or parenteral) of tetracycline are in the range of about 0.1 mg to 1 g per day. In a preferred embodiment, the transactivator is maintained in the "on" position by withholding tetracycline.

An estrogen-inducible system described by Braselmann, S. et al. *Proc Natl Acad Sci USA* (1993) 90:1657-61, is based on the fact that most mammalian cells neither express any Gal4-like activity nor endogenous estrogen receptor (ER), thus rendering estrogen an inert signal for them. The authors developed a selective induction system based on the estrogen-regulatable transcription factor Gal-ER. Gal-ER consists of the DNA-binding domain of the yeast Gal4 protein fused to the hormone-binding domain of the human ER and hence exclusively regulates a transfected coding sequence under the control of a Gal4-responsive promoter in mammalian cells. This system includes a synthetic Gal4-responsive promoter which consists of four Gal4-binding sites, an inverted CCAAT element, a TATA box, and the adenovirus major late initiation region. This promoter shows extremely low basal activity in the absence of, and high inducibility in the presence of, ligand-activated Gal-ER. The transcription factor Gal-ER is rendered more potent and less susceptible to cell type-specific variation by fusing the strong activating domain of the herpesvirus protein VP16 onto its C-terminus. In response to estrogen, e.g., 17-β estradiol, Gal-ER-VP16 induces the Gal4-responsive promoter at least 100-fold in, for example, transiently transfected NIH 3T3 and P19 cells. Rat fibroblast cell lines expressing integrated Gal-ER and Gal4-responsive fos genes were shown to be transformed in a strictly estrogen-dependent manner. The exogenous fos gene was rapidly induced to maximal levels within 1-2 hr of estrogen addition. Elevated Fos activity in turn stimulated transcription of the endogenous fra-1 gene. Thus, the Gal-ER induction system is a powerful genetic switch for regulating heterologous genes For induction of expression of the DNA molecules of the present invention in an estrogen inducible system in an animal, local or systemic treatment with estrogen would be required. An effective dose of an estrogen is a dose which would trigger the expression of an hHGF-encoding nucleic acid of the present invention to produce hHGF and promote growth of hHGF-expressing tumor cells. Such doses can be ascertained by one skilled in the art. Preferably, doses in the range of about 0.05 to 100 mg/kg of an estrogen are used in a single dose or in multiple doses over a period of about one week days to about 6 months, or even longer. Forms and preparations of estrogen and their usage in animals, particularly in humans, are well-known in the art (Hardman, J. G. et al., *Goodman and Gilman's The Pharmacological Basis of Therapeutics*, 10th Ed., McGraw-Hill Professional, New York, 2001, or subsequent edition). Estrogen analogues which are capable of specifically activating the exogenous transactivator while having fewer biological effects and side effects are preferred.

Ionizing radiation has been used to activate the transcription of exogenous genes, for example, encoding a cytotoxic protein TNF-I (Weichselbaum, R R et al., *Int J Radiation*

*Oncology Biol Phys* 24:565-67 (1992)) This may be accomplished through the use of radiation-responsive elements distal to the transcription start site of such genes. See, for example, Hallahan, D et al., *Proc Natl Acad Sci USA* 88:2152-20 (1991); Datta, R et al., *Proc Natl Acad Sci USA* 89:10149-53 (1992); Weichselbaum et al., supra; Hallahan, D E et al. *J Biol Chem* 268:4903-07 (1993); Weichselbaum, R R et al., *Intl J Radiation Oncology Bio. Phys* 30:229-34 (1994); Hallahan, D E et al. *Nature Med* 1:786-91 (1995), which references are hereby incorporated by reference in their entirety. Thus, the present invention provides methods for the spatial and temporal control of gene expression with such radiation-inducible promoters to activate hHGF.

The hHGF coding sequence is placed in a vector under control of a radiation-inducible promoter. In one embodiment, a genetic construct with a VP-16 DNA sequence that encodes a known powerful transactivating protein attached to the DNA coding sequence derived from the DNA binding domain or the Lac repressor is inserted downstream of Cis-acting elements which bind radiation-inducible proteins. These constructs are useful in amplifying radiation-induced signals. This construct would be cotransfected with the plasmid containing multiple DNA binding sites for the Lac repressor protein cloned upstream of genes which when activated alter the phenotypic response of tumors.

In one embodiment, hHGF or an active polynucleotide fragment thereof is recombined with a replication-deficient adenovirus type 5 (McGrory, et al. *Virology* 163:614-17 (1988)) to yield a vector designated Ad.Egr-hHGF (similar to the Ad.Egr-TNF vector made by GenVec, Rockville, Md., and described in Hallahan et al., 1995, supra). This vector employs the $CCA(A+T \text{ rich})_6 GG$ elements (known as "CArG" elements) within the 5'-untranslated region of the early growth response (Egr-1) promoter 425 bp upstream from the transcription start site (Datta et al., supra). A control region is containing the 6 CArG elements of the promoter/enhancer region of the Egr-1 gene is ligated upstream of the hHGF-encoding DNA. These control elements are known to be inducible in several types of human tumor cells. Other DNA sequences that activate transcription after X-irradiation and which may be used in the present method include AP-1 (Hallahan et al., 1993, supra) and the NKRB binding sequence (Brach, M. et al., *J. Clin. Invest.* 88:691-695 (1991)).

Cells that are to be transformed to express hHGF are injected with or otherwise administered, on one or on multiple occasions, about $2 \times 10^8$ PFU of AD5.Egr-hHGF. At an appropriate time thereafter, ranging from several hours to several days, or even weeks, the target tissue, is irradiated with a dose of X-irradiation effective to induce gene expression. The preferred radiation regimen can be determined readily by the skilled artisan using conventional clinical judgment. The dose and time course are a function of the particular promoter used and its responsiveness, and the objective. In one embodiment, 5 Gy X-irradiation are given four times per week for a total of 50 Gy, for example from a Maxitron generator (1.88 Gy/min).

An advantage of the foregoing method is that transcriptional activation of a promoter is controlled by ionizing radiation within a specific body volume and for a chosen period of time. This achieves both spatial and temporal regulation of hHGF transcription, promoting tumor growth to be induced at a desired time and in a desired volume of cells or tissue. Thus, cells which have incorporated and are capable of expressing the hHGF DNA but are not the intended targets of the induction are spared by excluding them from the volume being irradiated. In this manner, the radiation can be used for spatial hHGF-stimulated human tumor growth in a mammalian model.

Another generally applicable method is used in conjunction with gene therapy/gene delivery methods described below, for inducing activation of a gene of interest, in particular hHGF. This method is disclosed in detail in PCT publications WO94/18317, WO95/02684 and WO95/05389; Spencer, D. M. et al., *Science* 262:1019-1024 (1993); Travis, *Science* 262:989 (1993); and *Chem. & Eng. News*, Nov. 15, 1993, pp. 55-57, which references are hereby incorporated by reference in their entirety. This approach uses intracellular protein homodimerization, heterodimerization and oligomerization in living cells into which the hHGF DNA has been transfected. Chimeric responder proteins are intracellularly expressed as fusion proteins with a specific receptor domain. Treatment of the cells with a cell-permeable multivalent ligand reagent which binds to the receptor domain leads to dimerization or oligomerization of the chimeric receptor. In analogy to other chimeric receptors (see e.g. Weiss, *Cell* (1993) 73, 209), the chimeric proteins are designed such that oligomerization triggers the desired subsequent events, e.g. the propagation of an intracellular signal via subsequent protein-protein interactions and thereby the activation of a specific subset of transcription factors. The initiation of transcription can be detected using a reporter gene assay. Intracellular crosslinking of chimeric proteins by synthetic ligands allows regulation of the synthesis of hHGF and, thereby, selective induction of tumor growth.

In a preferred embodiment, the expression control sequence (either a ubiquitously acting expression control sequence or a tissue-specific one) is expressed in a regulatable fashion, meaning that it is preferably a component of any of a number of well-known regulatable expression systems.

Methods of making recombinant constructs are conventional. Such methods, as well as many other molecular biological methods used in conjunction with the present invention, are discussed, e.g., in Sambrook, et al. (1989), *Molecular Cloning, a Laboratory Manual*, Cold Harbor Laboratory Press, Cold Spring Harbor, N.Y.; Ausubel et al. (1995). *Current Protocols in Molecular Biology*, N.Y., John Wiley & Sons; Davis et al. (1986), *Basic Methods in Molecular Biology*, Elsevier Sciences Publishing, Inc., New York; Hames et al. (1985), *Nucleic Acid Hybridization*, IL Press; Dracopoli et al. *Current Protocols in Human Genetics*, John Wiley & Sons, Inc.; and Coligan et al. *Current Protocols in Protein Science*, John Wiley & Sons, Inc. See, also, the Examples herein.

In one embodiment, a recombinant construct of the invention is cloned into a suitable vector, such as a self-replicating plasmid or virus. This allows amplification of the construct, which can then be introduced into the embryonic cells with the vector sequences, or cleaved or otherwise removed from the vector sequences before introduction into embryonic cells. However, there is no requirement that the gene being introduced be incorporated into any kind of self-replicating plasmid or virus (Jaenisch, supra). In many cases, the presence of vector DNA has been found to be undesirable (Hammer et al. (1987) *Science* 235, 53; Chaka et al. (1985) *Nature* 314, 377; Chaka et al. (1986) *Nature* 319, 685; Kollias et al. (1986) *Cell* 46, 89; Shani, M. (1986) *Mol. Cell. Biol.* 6, 2624; Townes et al. (1985) *EMBO J.* 4, 1715.

A preferred use of the Tg animals of this invention is the study of tumor development, including the identification of pre-neoplastic lesions, if any, local tumor growth, invasion and metastasis. Furthermore, these Tg animals provide in vivo models for testing preventative or therapeutic measures for cancer. This includes preventing recurrence of tumor growth following the debulking or excision of a tumor. For example, the Tg animal can be administered a candidate anti-tumor agent, such as agents that inhibit hMet and/or hHGF expression and/or activity, or another type of treatment regimen. Such administration can be either concurrent with or preceding the implantation into the animal of a tumor cells or tissue. The ability of the test agent or regimen to inhibit growth of the implanted cells can then be measured. Tg animals of the invention (and cells derived therefrom) can also be used for testing therapeutic modalities such as chemotherapy, radiotherapy, immunotherapy and gene therapy. The Tg animals (and cells derived therefrom) can also be used to identify antineoplastic drugs which act to decrease the proliferation of tumor cells or the tumor dissemination, metastasis and growth of the metastatic tumor.

Human tumor xenografts can be introduced into (implanted into) a Tg animal (e.g., a mouse) of the invention by a variety of methods which will be evident to the skilled worker. These methods include, e.g., subcutaneous, intravenous or orthotopic introduction.

One class of anticancer agents that can be screened are oligonucleotides, particularly those designed to specifically inhibit a gene of interest. Examples of such oligonucleotides include ribozymes, anti-sense oligonucleotides, and double stranded nucleic acids used in methods of RNA interference (preferably siRNA molecules).

Ribozymes are RNA molecules that have an enzymatic or catalytic activity against sequence-specific RNA molecules. See, for example, *Intracellular Ribozyme Applications: Principles and Protocols*, J. Rossi et al., eds. (1999, Horizon Scientific Press, Norfolk, UK). Ribozymes have been generated against any number of RNA sequences such as target mRNAs, including calretinin, TNFα, HIV-1 integrase, and the human interleukins. Suitable ribozymes include RNA endoribonucleases (hereinafter "Cech-type ribozymes") such as the one which occurs naturally in *Tetrahymena thermophila* (known as the IVS, or L-19 IVS RNA) and which has been extensively described by Cech and collaborators (Zaug et al., (1984), *Science* 224, 574-78; Zaug et al., (1986), *Science* 231, 470-75; Zaug et al. (1986), *Nature* 324, 429-33; PCT Patent Publication No. WO 88/04300; and Been et al. (1986), *Cell* 47, 207-216). The Cech-type ribozymes have an eight base pair active site which hybridizes to a target RNA sequence after which cleavage of the target RNA takes place. The invention encompasses those Cech-type ribozymes which target eight base-pair active site sequences that are present in a target gene. See also U.S. Pat. No. 6,355,415 for methods of regulating gene expression with ribozymes.

Antisense oligonucleotides can be used to control gene expression through methods based on binding to DNA or RNA. Without wishing to be bound to any particular mechanism, types of antisense oligonucleotides and proposed mechanisms by which they function include, the following. The 5' coding portion of a polynucleotide sequence which encodes for a mature polypeptide of the present invention can be used to design an antisense oligonucleotide (RNA, DNA, PNA etc.) directed to any relevant target site, an ranging in length from about 10 to 40 bp. The antisense oligonucleotide can hybridize to mRNA and block translation (e.g., Okano, J. (1991), *Neurochem*. 56, 560; *Oligodeoxynucleotides as Antisense Inhibitors of Gene Expression*, CRC Press, Boca Raton, Fla. (1988)). Alternatively, an oligonucleotide can be made complementary to a region of the DNA involved in transcription (e.g., Lee et al.(1979), *Nucl. Acids Res* 6, 3073; Cooney et al (1988), *Science* 241, 456; and Dervan et al.(1991), *Science* 251, 1360), and prevent transcription and, thereby, synthesis of the protein. For further guidance on administering and designing antisense oligonucleotides, see, e.g., U.S. Pat. Nos. 6,200,960, 6,200,807, 6,197,584, 6,190,869, 6,190,661, 6,187,587, 6,168,950, 6,153,595, 6,150,162, 6,133,246, 6,117,847, 6,096,722, 6,087,343, 6,040,296, 6,005,095, 5,998,383, 5,994,230, 5,891,725, 5,885,970, and 5,840,708.

Inhibitory double stranded nucleic acids (interfering nucleic acids, or siNAs) can also be used to inhibit gene expression, using conventional procedures. Preferably the inhibitory molecule is an short interfering RNA (siRNA) molecule. Typical methods to design, make and use interfering RNA molecules are described, e.g., in U.S. Pat. No. 6,506,559, Tuschl et al. (1999) *Genes & Dev.* 13, 3191-3197; Kawasaki et al. (2003) *Nucleic Acids Res* 31:700-7; Miyagishi et al. (2003) *Nature Biotechnol* 20, 497-500; Lee et al. (2002) *Nature Biotechnol* 20:500-05, Brummelkamp et al. (2002) *Science* 296:550-53; McManus et al. (2002) *RNA* 8: 842-50; Paddison et al. (2002a) *Gene Dev* 16 948-58; Paddison et al. (2002) *Proc Natl Acad Sci USA* 99: 1443-48); Paul et al. (2002) *Nature Biotechnol* 20, 505-508; Sui et al. (2002) *Proc Natl Acad Sci USA* 99 5515-20; Yu et al. (2002) *Proc Natl Acad Sci USA* 99:6047-52; Hannon (2002) *Nature* 418: 244-51; Bernstein et al. (2002) *RNA* 7:1509-21; Hutvagner et al., *Curr. Opin. Genetics & Devel* 12:225-2; Brummelkamp (2002) *Science* 296:550-53; Lee et al. (2002) *Nature Biotechnol* 20:500-505; Miyagishi et al. (2002) *Nature Biotechnol.* 20:497-500; Paddison et al. (2002) *Genes & Dev* 16:948-58; Paul et al. (2002) *Nature Biotechnol.* 20, 505-508; Sui et al. (2002) *Proc Natl Acad Sci USA* 99: 5515-20; Yu et al. (2002) *Proc. Natl. Acad. Sci. USA* 99:6047-52; Allshire (2002) *Science* 297:1818-19; Volpe et al. (2002) *Science* 297:1833-37; Jenuwein (2002) *Science* 297:2215-18; Hall et al. (2002) *Science* 297 2232-2237; Hutvagner et al. (2002) *Science* 297: 2056-60; McManus et al. (2002) *RNA* 8:842-850; Reinhart et al. (2002) *Gene & Dev.* 16:1616-26; Reinhart et al. (2002) *Science* 297:1831; Fire et al. (1998) *Nature* 391:806-11, Moss (2001) *Curr Biol* 11: R772-5, Brummelkamp et al. (2002) *Science* 296:550-3; Bass (2001) *Nature* 411 428-429; Elbashir et al. (2001) *Nature* 411:494-98; U.S. Pat. No. 6,506,559; US Pat. publication 20030206887; and PCT publications WO99/07409, WO99/32619, WO 00/01846, WO 00/44914, WO00/44895, WO01/29058, WO01/36646, WO01/75164, WO01/92513, WO 01/29058, WO01/89304, WO01/90401, WO02/16620, and WO02/29858. For reviews on inhibitory RNAs, see also Lau et al. (2003) *Sci Amer*, pp. 34-41; McManus et al. (2002) *Nature Rev Genetics* 3:737-747; and Dykxhoorn et al. (2003) *Nature Rev Mol Cell Biol* 4:457-67.

Antisense oligonucleotides, ribozymes, or siRNAs can be composed of modified oligonucleotides for improved stability, targeting, etc., and are delivered to cells which express the target gene in vivo. A preferred method of delivery involves using a DNA construct encoding a ribozyme. etc., under the control of a strong constitutive pol III or pol II promoter, so that transfected cells will produce sufficient quantities of the ribozyme to destroy endogenous target gene messages and/or inhibit translation.

Another class of agents that can be screened for possible use as drugs are "small molecules," also referred to herein as "compounds," which are isolated from natural sources or made synthetically. In general, such molecules may be identified from large libraries of natural products or synthetic (or semi-synthetic) extracts or chemical libraries according to methods known in the art. Those skilled in the field of drug discovery and development will understand that the precise source of test extracts or compounds is not critical to the methods of the invention. Accordingly, virtually any number of chemical extracts or compounds can be used in the methods described herein. The types of extracts or compounds that may be tested include plant, fungal, prokaryotic or eukaryotic cell or organism-based extracts, fermentation broths, and synthetic compounds including modifications of existing compounds. Numerous methods are also available for generating random or directed synthesis (e.g., semi-synthesis or total synthesis) of any number of chemical compounds, including, but not limited to, saccharides, lipids, peptides, polypeptides and nucleic acids and derivatives thereof. Synthetic compound libraries are commercially available, e.g., from Brandon Associates (Merrimack, N.H.) and Aldrich Chemical Co. (Milwaukee, Wis.).

Alternatively, libraries of natural compounds in the form of bacterial, fungal, plant, and animal extracts are commercially available from a number of sources, e.g., Biotics (Sussex, UK), Xenova (Slough, UK), Harbor Branch Oceanographic Institute (Ft. Pierce, Fla.), and PharmaMar USA (Cambridge, Mass.). In addition, natural and synthetically produced libraries can be generated according to methods known in the art, e.g., by standard extraction and fractionation methods. Furthermore any library or compound may readily be modified using standard chemical, physical, or biochemical methods.

Another class of agents that can be screened are antibodies, e.g., those specific for the Met or hHGF. Any of a variety of sources of antibodies and antigen-binding fragments thereof (e.g., Fab, and $F(ab')_2$) can be used in such methods. Such antibodies may be in the form of whole or fractionated antisera, isolated polyclonal antibodies as well as mAbs, recombinant, humanized or partially humanized mAbs, single chain antibodies (scFv). The antibodies or fragments can be of any isotype, e.g., IgM, various IgG isotypes such as $IgG_1 \cdot IgG_{2a}$, etc., and they can be from any antibody-producing animal species including goat, rabbit, mouse, chicken or the like.

Antibodies can be prepared according to conventional methods. See, e.g., Green et al., In: *Immunochemical Protocols* (Manson, ed.), (Humana Press 1992); Coligan et al., in *Current Protocols in Immunology*, Sec. 2.4.1 (1992); Kohler & Milstein, Nature 256:495 (1975); Coligan et al., sections 2.5.1-2.6.7; and Harlow et al., *Antibodies: A Laboratory Manual* (Cold Spring Harbor Laboratory Pub. 1988). Methods of preparing humanized or partially humanized antibodies, and antibody fragments, and methods of purifying antibodies, are conventional.

For preparation of mAbs, any technique which provides antibodies produced by continuous cell line cultures can be used. Examples include, e.g., the hybridoma technique (Kohler et al., supra), trioma techniques, human B-cell hybridoma technique (Kozbor et al., 198, *Immunol Today* 4:72), and the EBV-hybridoma technique, to produce human mAbs (Cole, et al., In: *Monoclonal Antibodies and Cancer Therapy*, Alan R. Liss, Inc., 1985, pp. 77-96).

Techniques described for the production of single chain antibodies (e.g., U.S. Pat No. 4,946,778) can be adapted to produce single chain antibodies to the polypeptides of interest in this invention. Also, Tg animals may be used to express partially or fully humanized antibodies to immunogenic polypeptide products of this invention.

Another useful form of antibody for the present invention is the intracellular antibody or "intrabody". See, for example, Marasco (1997) WA, *Gene Ther.* 4:11-15. Intrabodies are expressed and act intracellularly, as a form of gene therapy for cancer and control of infectious diseases.

Agents to be evaluated can be introduced into Tg animals of the invention by conventional methods. For example, nucleic acids, such as antisense RNA, ribozymes, RNAi, or DNA constructs encoding a peptide or protein agent of interest, etc., can be introduced by transfection or electroporation. Electroporation can also be used to introduce other large molecules, such as proteins, including antibodies, into a cell.

Any of the methods or assays described herein can, of course, be adapted to any of a variety of high throughput methodologies, as can the generation, identification and characterization of putative anti-cancer agents. High throughput assays are generally performed on a large number of samples, and at least some of the steps are performed automatically, e.g., robotically. High throughput screening systems are widely available. For example, microfluidic technologies are available from Agilent/Hewlett Packard (Palo Alto, Calif.) and Caliper Technologies Corp. (Mountain View, Calif.).

In some embodiments, methods of the invention involve the simultaneous analysis of a plurality of test agents. For example, at least about 2, about 5, about 10, about 20, about 50, about 100, about 500, about $10^3$, about $10^4$ or more biological entities can be analyzed simultaneously.

Having now generally described the invention, the same will be more readily understood through reference to the following examples which are provided by way of illustration, and are not intended to be limiting of the present invention, unless specified.

EXAMPLE I

Materials and Methods

Cell Lines and Tumors

The following cell and tumor lines were used: S-114 are NIH-3T3 murine cells transformed with hHGF hMet (Rong S et al. (1993) *Cell Growth Differ* 4:563-69) and M-114 are NIH-3T3 murine cells transformed with murine HGF ("mHGF") and murine Met ("mMet"). The above two lines were grown in DMEM supplemented with 8% calf serum (v/v). SK-LMS-1 is a human leiomyosarcoma cell line in which hMet and hHGF function in an autocrine manner (Jeffers et al. (supra). These cells were maintained in DMEM supplemented with 10% fetal bovine serum (v/v). DA3 is a mouse mammary carcinoma cell line expressing mMet (Firon M et al. (2000) *Oncogene* 19:2386-97); these cells were grown in DMEM supplemented with 10% fetal bovine serum (v/v) and antibiotics. 121-1TH-14 cells are NIH-3T3 murine cells transformed with hMet. Okajima cells are human gastric carcinoma cells expressing Met (Faletto D L et al. (1993) *Experientia Suppl.* 65:107-30). Parental DBTRG-05MG (DB-P) cells were obtained from the American Type Culture Collection (ATCC Cat. No. CRL-2020) and cultured in DMEM containing 10% FBS). To isolate proliferative subclones from DB-P, cells were plated at low density in DMEM supplemented with HGF/SF for 3 weeks and fast-growing colonies derived from single cells were subjected to further analysis. The DB-A2 subclone was selected (as described below) since it was most active in $^3$H-thymidine incorporation assays in response to HGF/SF and showed differences in downstream signaling.

Human HGF/SF Transgene

The human HGF plasmid clone pBS7-3 (S. Rong et al., 1992, supra) was cut with BamH1 and Sa11 and the insert fragment was blunt-ended with Klenow DNA polymerase 1. This DNA fragment, with the entire cDNA open reading frame was ligated into Nru1 cut mouse metallothionein promoter vector 2999 obtained from R. Palmiter (M. Jeffers et al. (1998) *Proc Natl Acad Sci USA* 95:14417-22) and used as a transgene for producing HGF/SF scid mice, as described below. The transgene is shown schematically in FIG. 1A.

Genotyping hHGF/SF Tg Mice

Genomic DNA isolated from animal tails was used for genotyping hHGF Tg mice by polymerase chain reaction (PCR) as described (Sambrook, J. et al., *Molecular Cloning: A Laboratory Manual,* 2nd Edition, Cold Spring Harbor Press, Cold Spring Harbor, N.Y., 1989). The following primer pair was used:

5'-AGTCTGTGACATTCCTCAGTG-3' (sense strand, nt. 731-751) (SEQ ID NO:1) and
5'-TGAGAATCCCAACGCTGACA-3' (antisense strand, nt. 1110-1130) (SEQ ID NO:2), representing sequences in hHGF cDNA (Accession Number: X16323).

The following CDNA sequence is preferred (see Rong et al., Molec. Cell Biol., 1992, supra):

```
   1 cacacaacaa acttagctca tcgcaataaa aagcagctca gagccgactg gctcttttag
  61 gcactgactc cgaacaggat tctttcaccc aggcatctcc tccagaggga tccgccagcc
 121 cgtccagcag caccatgtgg gtgaccaaac tcctgccagc cctgctgctg cagcatgtcc
 181 tcctgcatct cctcctgctc cccatcgcca tccctatgc agagggacat aagaaaagaa
 241 gaaatacaat tcacgaattc aaaaaatcag caaagactac cctaatcaaa atagatccag
 301 cactgaagat aaaaaccaaa aaagtgaata ctgcagacca atgtgctaat agatgtacta
 361 ggaataatgg acttccattc acttgcaagg cctttgtttt tgataaagcg agaaaacaat
 421 gcctctggtt cccctttcaat agcatgtcaa gtggagtgaa gaaagaattt ggccatgaat
 481 ttgacctcta tgaaaacaaa gactacatta gaaactgcat catcggtaaa ggacgcagct
 541 acaagggaac agtatctatc actaagagtg gcatcaaatg tcagccctgg agttccatga
 601 taccacacga acacagcttt ttgccttcga gctatcgggg taaagaccta caggaaaact
 661 actgtcgaaa tcctcgaggg gaagaagggg gaccctggtg tttcacaagc aatccagagg
 721 tacgctacga agtctgtgac attcctcagt gttcagaagt tgaatgcatg acctgcaatg
 781 gggagagtta tcgaggtctc atggatcata cagaatcagg caagatttgt cagcgctggg
 841 atcatcagac accacaccgg cacaaattct tgcctgaaag atatcccgac aagggctttg
 901 atgataatta ttgccgcaat cccgatggcc agccgaggcc atggtgctat actcttgacc
 961 ctcacacccg ctgggagtac tgtgcaatta aaacatgcgc tgacaatact gtaaatgata
1021 ctgatgttcc tatggaaaca actgaatgca tccaaggtca aggagaaggc tacaggggca
1081 ctgccaatac catttggaat ggaattccat gtcagcgttg ggattctcag tatcctcaca
1141 agcatgacat gactcctgaa aatttcaagt gcaaggacct acgagaaaat tactgccgaa
1201 atccagatgg gtctgaatca ccctggtgtt ttaccactga tccaaacatc cgagttggtt
1261 actgctccca aattccaaac tgtgatatgt caaatggaca agattgttat cgtgggaatg
1321 gcaaaaatta tatgggcaac ttatcccaaa caagatctgg actaacgtgt tcaatgtgga
1381 acaagaacat ggaagactta caccgtcata tcttctggga accagatgca agtaagctga
1441 atgagaatta ctgccgaaat ccagatgatg atgctcatgg accctggtgc tacacgggaa
1501 atccactcat tccttgggat tattgcccta tttctcgttg tgaaggtgat accacaccta
1561 caatagtcaa tttagaccat cctgtaatat cttgcgccaa aacgaaacaa ctgcgagttg
1621 taaatgggat tccaacacga acaaatgtag gatggatgat tagtttgaga tacagaaata
1681 aacatatctg cggaggatca ttgataaagg aaagttgggt tcttactgca cgacagtgtt
1741 tcccttctcg agacttgaaa gattatgagg cttggcttgg aattcatgat gtccatggaa
1801 gaggagagga gaaacgcaaa caggttctca atgtttccca gctggtatat ggccctgaag
1861 gatcagatct ggttttaatg aagcttgcca gacctgctgt cctggatgat tttgttaata
1921 caattgattt acctaattat ggatgcacaa ttcctgaaaa gaccagttgc agtgtttatg
1981 gctggggcta cactggattg atcaactatg atggtctatt acgagtggca catctctata
2041 taatgggaaa tgagaaatgc agccagcatc accgagggaa ggtgactctg aatgagtctg
2101 aaatatgtgc tggggctgag aagattggat caggaccatg tgagggggat tatggtggcc
```

-continued

```
2161  cacttgtttg tgagcaacat aaaatgagaa tggttcttgg tgtcattgtt cccggccgtg
2221  gatgcgccat tccaaatcgt cctggtattt ttgtccgagt agcatattat gcaaaatgga
2281  tacacaaaat tattttaaca tataaggtac cacagtcata gctgaagtaa gtgtgtctga
2341  agcacccacc aatacaactg tcttttacat gaagatttca gagaatgtgg aattaaaaat
2401  accacttaca acaatcctaa gacaactact ggagagtcat gtttgttaaa attctcatta
2461  atgtttatgg gtgttttctg ttgttttgtt tgtcagtgtt attttgtcaa tgttgaagtg
2521  aattaaggta catgcaagtg tagtaacata tctcctgaag atacttgaat ggattaaaaa
2581  aacacacagg tataattgct ggataaagat tttgtgggga aaaaatcaat taatctctct
2641  aagctgcttt ctgaggttgg tttcttaata atgagtaaac cataaattaa atgttatttt
2701  aacctcacca aaacaattta taccttgtgt ccttaaattg taccctatat taaattatat
2761  tacatttcat atgctatatg ttatagttca ttcatttctc ttcaccatgt atcctgcaat
2821  actggtacac gaacacactt tttacaaaac cacatacccca tgtacacatg cctaggtaca
2881  catgtacatg cactacagtt taaattatga tgtacttaat gtaacctcta aatattttag
2941  aagtatgtac ctatagtttt acctcaaaaa aatagaaatc tctaaagacc agtagaaata
3001  ttaaaaaatg atgcaaaatc aaaatgagtg gctaattctc catacgtaat ctgcagatga
3061  tcttctctgg ttgacatttt acgtgtggcc atcaccccgg gttaaataac acctaatcta
3121  ggtgtttaca tgtattcaat atcctagttt gtttcatgta gtttctaatt cttaaaggaa
3181  agagggtaat aattctattt gtgtaatttg tttcctccaa acttaaggcc acttatttac
3241  acaagatatt tgtatgtcta ctttcctaaa gcatttcttc agtgctcaga tcagtgtcta
3301  attgaagaag attaaaactg ctttggtcat taaaaacgta tttaaatagg ttaattctaa
3361  gacttgctgc tgtgattgac ttctagctca ctgcctttaa attttaaaaa atttaagagg
3421  aaaattttca tgtctccaaa gttttataaa tacccttcat caagtcatgc attaaagtat
3481  atattagaga aaaaaaaata ctttttctcaa cctggaagat tttagcctaa taaagttttt
3541  ttgaagtaaa agaaaacttg taaagggaaa gaaactagtt tgtctaaact ctgtattcat
3601  tttttttttt tttgaagtac agtggaatct gttgaatcag atattttatc aagatatctt
3661  tatttttttct tatttcattt ttacaaagat cactcccaat gccatatgta atagacattt
3721  aaatttcgtg ttctgtatga cagccaaatg atcatattta tcattgtatt tgtcatgttt
3781  agctaaaaat catgtattgt tgagaaatag aataacaaaa agtaatagga taggctttga
3841  atttttgcaa aaaatcttcc tgtacaaaac atcttaaaaa ataatttttt gagtggtgtg
3901  aatctagtat tcccatttct ctgatttagt tttcttgagt gattttatc aaggctaagt
3961  ccccaaatga ttccctaaca gctctttaga ataccgttta atctggacta aaatggtttt
4021  aagtttatgg agagtttagt ccacagaact aactggactt ctggcggcaa gtccagaaat
4081  gcttatacaa atttttttttt cataataaga tatgtgctgg tatcaaggaa cttaaagtgg
4141  aagcaaaaag acatccaagt agttgctagt ctccatcatc ttatctgatt gtatttctct
4201  tttccttata taatacacca ttttcataag aacacctaga aatttcaaga gtatattgcc
4261  aaaatataaa gtatatttcc tagtttcttc tggctgaacc agtgaaattt tattgttgca
4321  tattaatgat atctttaaaa cttttataaa aattgtcata cttttaaata ctcacatttt
4381  aaaaatactt cttttatgac tcttcctcta aatttcctgg aaatacagat aaagattagc
4441  tagatacaag atgcagctaa gtatttagac attttgagcc cagtattttt cattttatta
4501  aaggctaaaa acaataccac caataaaatca tcaaacaaac tgtacaaaat aattctgtct
```

```
4561  ttgggaggct cctttgtga tagagggaca tgggtggaat tgacaatgaa agttagatga 4621  acaaggtccg tgttatttta ggtagtagaa cagggtagag tcatgtcatt atttgcgggc 4681  ggaagatact atttaccacg tgttctttgc tgaatcaatt attaaacatt tttaaaaatc 4741  caattatcca ctttattttg tgtcattgac aaaaggatct tttaagtcag aggtttcaat 4801  gtgatttttg gcttggctgt ttgaataatg gttatgtact gttataattg tagacatttt 4861  ctcatgtcta ccaggaattg aagtgtaaaa ctaaatatt tttcataatg cctctgccgt 4921  gcggaaggaa tgataatcct tttgtatact tctttaattt tattgtaaaa tgtgtaatga 4981  cttttaccta tatgctgtgg gcaggtcctc agtaaaatct attgagtcaa tttctagtat 5041  taataggctt ttgcttgcta tctaagtgtt tcaaattatg ggaagtgtga gacactggaa 5101  ggcaagaaaa ttaacaataa tggcatgtga tagcaaaatt gtatttcact tattcctgtg 5161  aatatttctt gttggtacca atggtactgt acaaagtgaa tgttatagcc acaacattct 5221  cttgaaaaga acactgtcaa gaagtgggaa attgctgtca ggcatttcgt tgttgttttt 5281  aaactttta aaaagaaat actggtttg caagatagag atcatgaggt aaataatttt 5341  aataagctct tatactaaaa agccttaaat cgatttactg agattcaaaa catactatta 5401  taatcaatta tatcccatat atgtaggcaa actcatttaa aaaataaaat taattttggt 5461  aaaagtacat agtgtttgtt tttaaaatac ataattttaa aataaatcgc ttgtcatgat 5521  aaagtccaaa aagaagttat cttcaatat tcaactaagt ttggagctaa gaatttacta 5581  atacaaaaaa aagttaaaat gttttggacc atatatatct tgacagtgta acttttaagt 5641  aggctcattt ccatttgcac agaaagtttc tgtctttagg aaactgaaaa tgaaatactg 5701  tggatgttat gactgtttgt cttctatgta aataggaaat taataagctg cctattgagt 5761  ggtatagctg tatgcttacc caaaaaggg aacactgtgg ttatgacttg tattataaac 5821  tttctgtagt taataaagtt gttatttta taaccatgat tatatattat tattaataaa 5881  atattttatc gaaatgct (SEQ ID NO: 3)
```

These sequences are unique to hHGF transgene that is driven by Metallothionein (MT) promoter in the construct used for generating Tg mice (Jeffers et al. (supra)).

RNA Preparation and Reverse Transcription-Polymerase Chain Reaction (RT-PCR)

Total RNAs were isolated from different mouse tissues using TRIzol reagent (Invitrogen). For detection of hHGF expression in various tissues from C3H scid mouse, RT-PCR was performed by using "One-step RT-PCR" (Invitrogen) with the primer pair specific for hHGF:

5'-AAACGCAAACAGGTTCTCAATG-3' (sense) (SEQ ID NO:4) and

5'-CTATGACTGTGGTACCTTATATG-3' (antisense) (SEQ ID NO:5).

For comparing the expression of hHGF transgene in C3H scid background to that in B6 background, RT was performed using 1 μg of total RNA and the SuperScript™ II RNase H⁻ Reverse Transcriptase (Invitrogen). One microliter of RT product was then used for PCR amplification of hHGF or β-actin. In the later case, the primers used for detection of hHGF are 5'-CAGCGTTGGGATTCTCAGTAT-3' (sense) (SEQ ID NO:6) and 5'-CCTATGTTTGTTCGTGTTGGA-3' (antisense); (SEQ ID NO:7)

and the primers used for detection of human β-actin are

5'-CGTGACATCAAAGAGAAGCTGTG-3' (SEQ ID NO: 8) (sense)

and

5'-GCTCAGGAGGAGCAATGATCTTGA-3' (SEQ ID NO: 9) (antisense).

The RT-PCR products were electrophoresed in a 2% agarose gel and visualized by staining with ethidium bromide.

Immunoprecipitation and Western Blot Analysis

Cell extracts were prepared from the mouse livers by homogenized in RIPA buffer consisting of 20 mM Tris-HCl (pH 7.5), 150 mM NaCl, 1% Nonidet P-40, 0.5% deoxycholate, 0.1% SDS, 1 mM EDTA, 50 mM NaF, 1 mM sodium orthovanadate, and complete proteinase inhibitor cocktail tablets (Roche Applied Science). DC Protein Assay (Bio-Rad) was used to quantify the protein concentrations. 400 μg of protein extracts were incubated with anti-hHGF/SF mAb (A-7) (Cao et al., supra) at 4° C. for overnight. The immunoprecipitated complexes were collected by protein G sepharose beads (Amersham Biosciences), eluted in 1× Laemmli buffer (Sigma), separated in 10% Tris-Gly gel (Invitrogen) and blotted onto PVDF membrane (Invitrogen). The Western blot analysis was performed using the anti-hHGF mAb.

Heparin Beads Pull-Down Assay

Liver homogenate (1 mg) was incubated with heparin-conjugated beads (Heparin immobilized on cross-linked 4% beaded agarose; Sigma) at 4° C. for 2 hr. Heparin-bound HGF/SF was eluted in 1×Laemmli buffer, separated on a 12% SDS-PAGE gel and Western blot was detected by anti-hHGF/SF antibody.

Sandwich ELISA for Detection of Serum hHGF/SF 96-well microplates (EIA plates) were coated with a mixture of anti-hHGF antibodies A-1, A-5, A-7 and A-10 (10 pg/ml total final concentration) (Cao et al., supra) in 50 µl of Coating Buffer (0.2M $NaHCO_3/Na_2CO_3$, pH9.6) and were incubated at 4° C. overnight. The next day the coated plates were washed twice with Wash Buffer (1×PBS with 0.05% of Tween-20) and blocked with Blocking Buffer (1×PBS with 1% of BSA, pH7.4) at 4° C. for overnight (200 µl/well). Human HGF/SF standards were prepared at 0.5, 1.0, 1.5, 2.0, 2.5, 3.0, 3.5 ng/ml in Blocking Buffer. Serum samples from HGF/SF Tg and control scid mice were diluted with same volume of Blocking Buffer. The diluted standards and samples were added to coated and blocked EIA plate (50 µl/well) at 4° C. for overnight. Plates were washed twice in Wash Buffer and rabbit anti-hHGF polyclonal antibody (Dr. Brian Cao's Lab) was added to the wells at 1:1000 dilution from 2 mg/ml stock in Blocking Buffer followed by incubation at room temperature for 1.5 hours. Plates were washed twice again and alkaline phosphatase-coupled goat anti-rabbit IgG (Sigma) was added (50 µl/well) at 1:2000 dilution in Blocking Buffer for 1.5 hours at RT. After washing four times in Wash Buffer, phosphatase substrate CP-nitrophenyl phosphate was added for 30 min, and absorbance was measured at 405 nm. HGF concentration of the serum samples was determined by the standard curve.

Human Tumor Cell Lines

The human leiomyosarcoma cell line SK-LMS-1 and human glioblastoma cell line U118 were cultured in DMEM (Invitrogen) supplemented with 10% fetal bovine serum. The human prostate cancer cell line DU145 and human melanoma cell line M14 were cultured in RPMI (Invitrogen) supplemented with 10% or 5% fetal bovine serum, respectively.

Tumorigenicity

Human tumor cells were suspended in serum-free DMEM or RPMI accordingly at the concentration of $5-10 \times 10^5$ cells/ml. For each mouse, 100 µl of cell suspension was implanted subcutaneously (sc) implanted into the right side of the back. For each tumor cell line, the same number of scid control mice and HGF/SF Tg scid mice (5-10 mice for each group) were used. After implantation, mice were monitored and the tumor sizes were measured twice a week.

EXAMPLE II

Production of hHGF/SF Tg scid Mice

The production of hHGF Tg scid mice is schematically represented in FIG. 1B. To create Tg mice expressing hHGF ligand, an expression vector carrying hHGF cDNA driven by the mouse metallothionein-1 (MT) gene promoter (FIG. 1A) was microinjected into C3H/B6 mouse embryos. Presence of the hHGF transgene in mice was determined by PCR-based genotyping using primers specific for the transgene. The derived hHGF-Tg mice were then crossed onto mice homozygous for the scid mutation, the presence of which was determined by the absence of mouse IgG. hHGF Tg mice with scid backgrounds were obtained by backcrossing the Tg mice produced as above to C3H scid/scid homozygotes for ten generations to obtain mice congenic for hHGF on the C3H scid background (FIG. 1B). One characteristic phenotypic trait present in all hHGF Tg scid mice was a black tail (from the B6 progenitor), which is easily distinguished from the brown tails of the C3H scid mice that did not pick up the transgene.

EXAMPLE III

Expression of hHGF/SF in Tg scid Mice

Figure 2A:
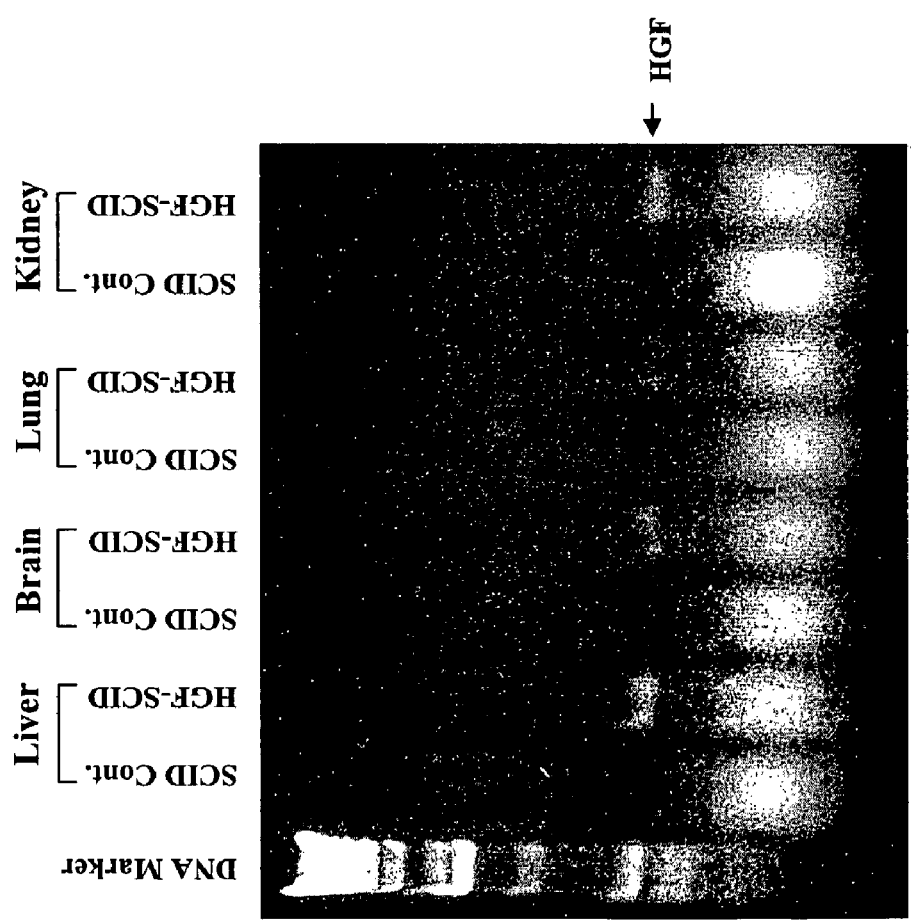
Figure 3:
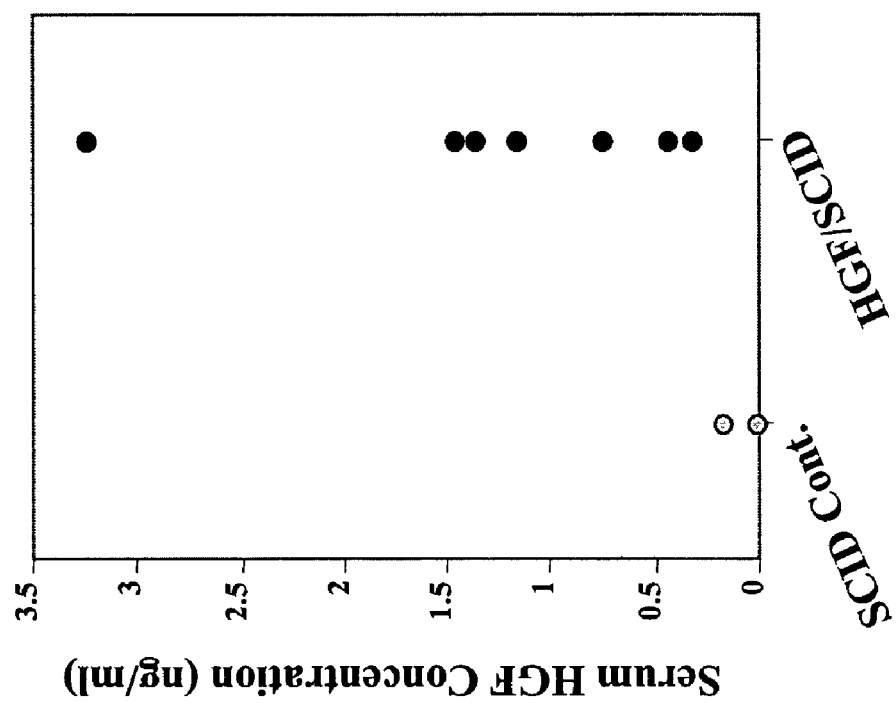
FIG. 3 shows high levels of HGF/SF in the serum of scid mice transgenic for hHGF. Mouse sera were obtained from a control and HGF/SF Tg scid mice, and concentrations of HGF/SF were determined using sandwiched ELISA with anti-hHGF/SF antibody.

To determine whether the hHGF transgene was expressed, RNA samples were prepared from different tissues of both "control" scid mice and hHGF Tg scid mice. By RT-PCR analysis using primers specific for hHGF, it was determined that hHGF transcripts were expressed in a wild range of tissues including liver, brain, lung and kidney (FIG. 2A). The presence of the hHGF protein was also confirmed in livers of the hHGF Tg scid mice by immunoprecipitation and Western Blot analysis using antibodies against hHGF (FIG. 2B). A significant amount of hHGF ligand was also detected in the circulating blood of the hHGF Tg scid mice as determined by sandwich ELISA using the same antibodies (Table 1/FIG. 3). Thus, the hHGF ligand is expressed in the hHGF Tg scid mice.

TABLE 1

| SCID Control Mice | | HGF/SCID Mice | |
|---|---|---|---|
| Mouse No. | Serum HGF (ng/ml) | Mouse No. | Serum HGF (ng/ml) |
| 1 | 0 | 1 | 1.45 |
| 2 | 0 | 2 | 3.24 |
| 3 | 0 | 3 | 0.43 |
| 4 | 0 | 4 | 1.35 |
| 5 | 0 | 5 | 0.31 |
| 6 | 0.16 | 6 | 1.16 |
| 7 | 0 | 7 | 0.74 |

EXAMPLE IV

Higher Expression of hHGF/SF Transgene in C3H scid Mice Than in B6 Mice

Previously, a Tg mouse overexpressing murine HGF/SF has been generated and found to have a large liver compared to non-Tg controls on an FVB background (Sakata, H et al., supra).

Figure 4A:
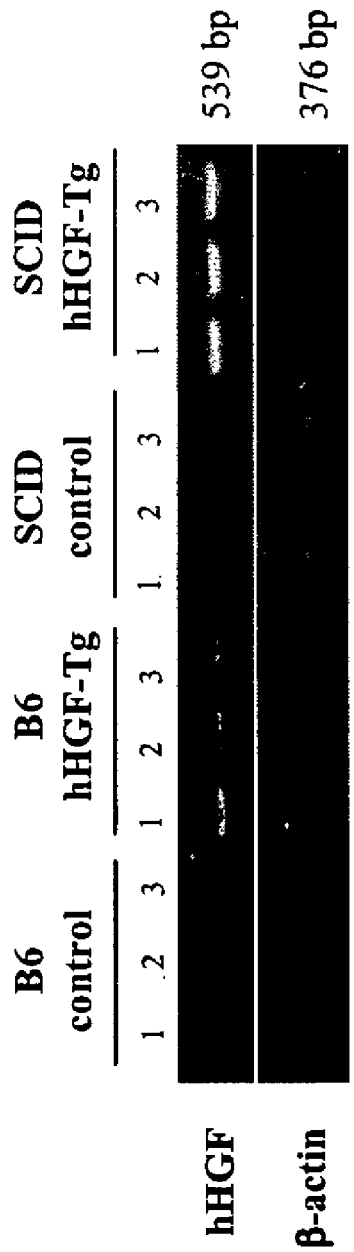
FIGS. 4A-4B show differential expression of hHGF transgene in C3H scid and B6 mice.
Figure 4B:
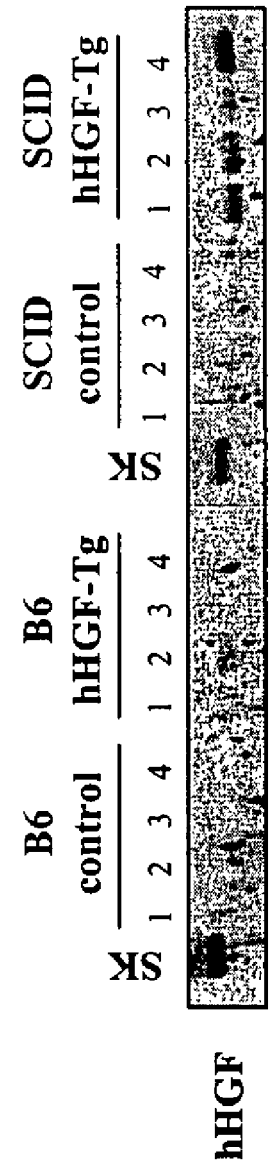

The hHGF Tg mice on the B6 background displayed minimal changes in liver size. To understand whether the difference in liver size between animals Tg for murine vs. hHGF Tg mice was due to difference in the background mouse strains, the expression of hHGF transgene in mice of the B6 background was compared to mice of the C3H (+scid) background. Interestingly, C3H scid Tg mice showed much higher levels of hHGF expression and displayed significantly larger livers than B6 Tg mice (see, e.g., FIGS. 4A-4B), suggesting that difference in the genetic background might affect transgene expression. This prompted the inventors to generate the Tg mice that are congenic with C3H scid animals as is schematically presented in FIG. 1B.

EXAMPLE V

Enhanced Met-Mediated Tumor Growth in hHGF/SF Tg scid Mice

Having generated a hHGF Tg scid mouse, the inventors examined whether these animals supported growth of Met+ human tumors in vivo better than did normal scid counterparts. Several human tumor cell lines with or without Met expression were tested.

Figure 5:
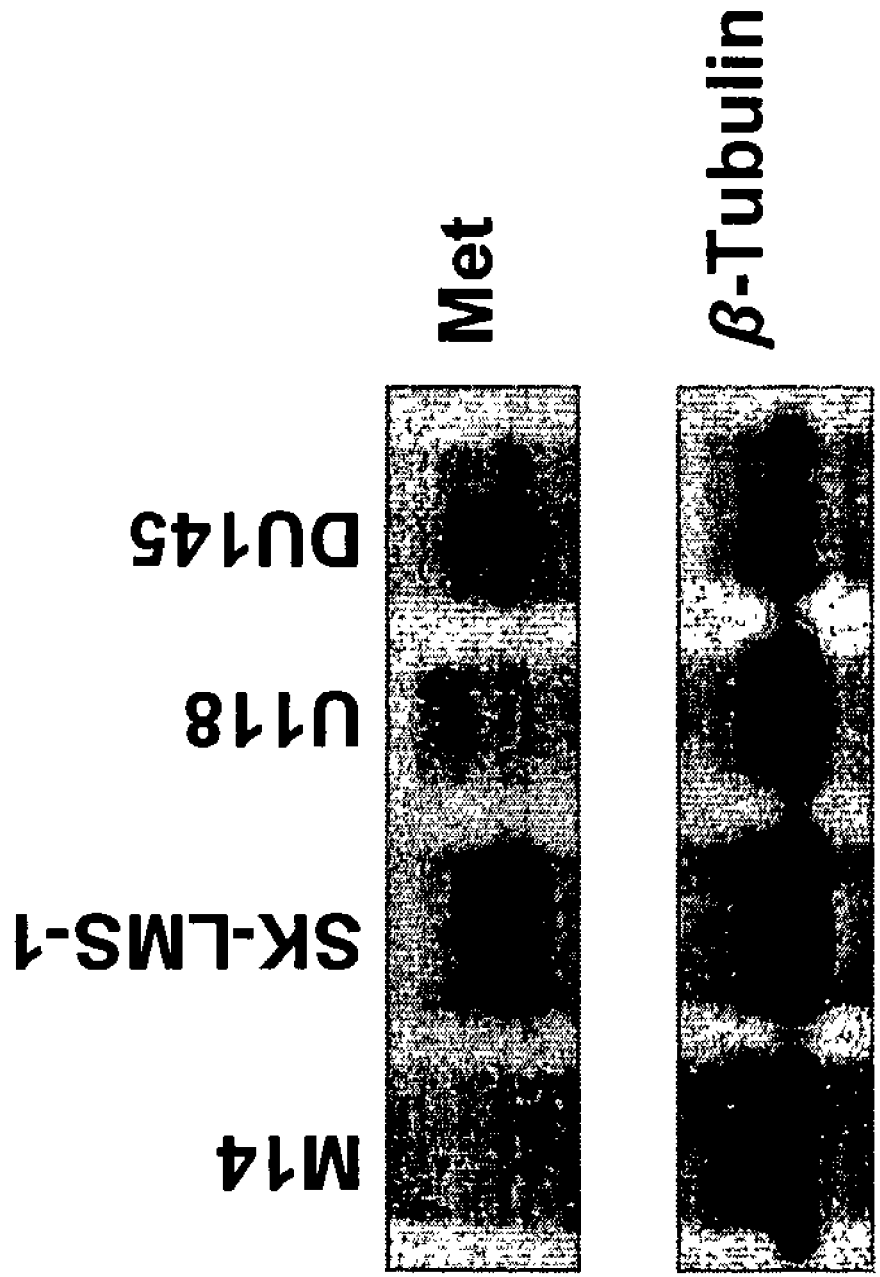
FIG. 5 shows Met receptor expression in different human tumor cell lines. Whole cell extracts were prepared from M14, SK-LMS-1, U118 and DU145 cells, and Western blots were detected by anti-Met (C-28) and anti-β tubulin (D-10) antibodies.
Figure 6:
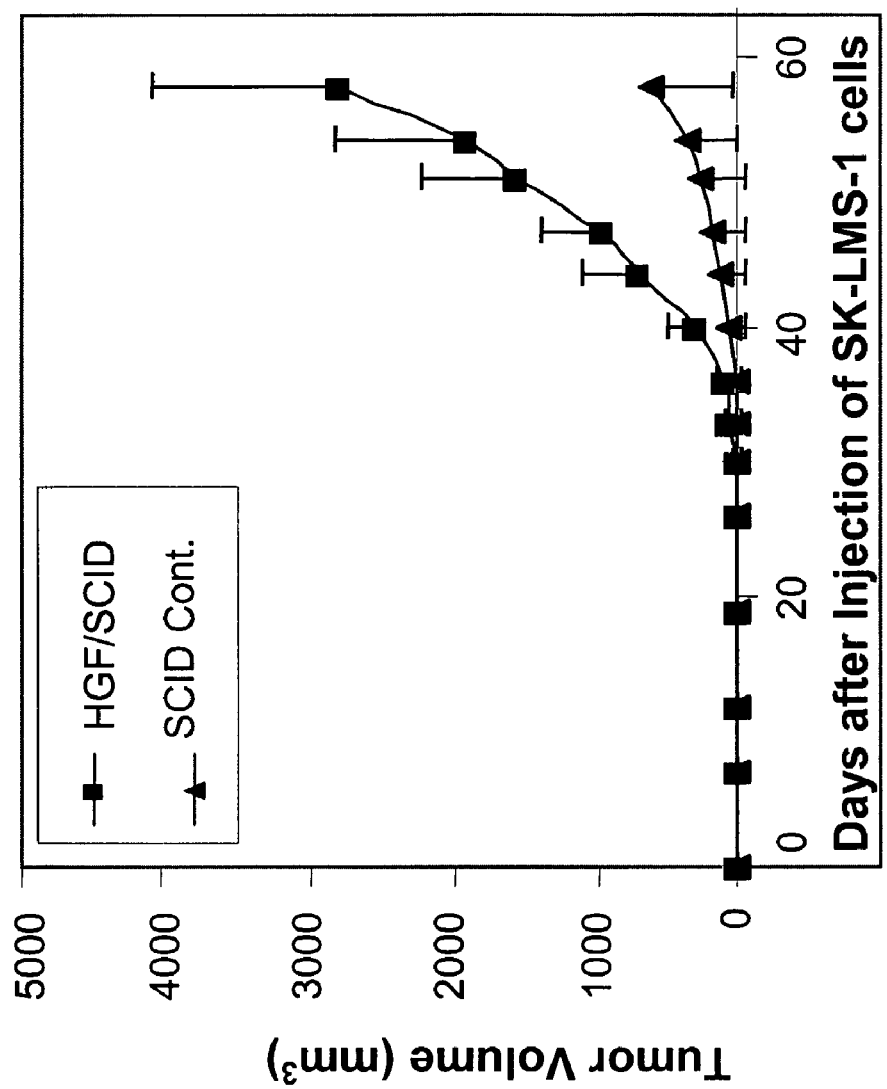
FIG. 6 shows enhanced tumor growth of SK-LMS-1 human tumor xenografts in hHGF Tg scid mice. Equal numbers of cells ($5 \times 10^5$/mouse) were subcutaneously implanted into the backs of the control scid and the hHGF Tg scid mice. The tumor growth was monitored twice a week. The tumor volumes are mean values of 6 tumors derived from each animal group (p=0.002; Student's t test: p=0.002).
Figure 7:
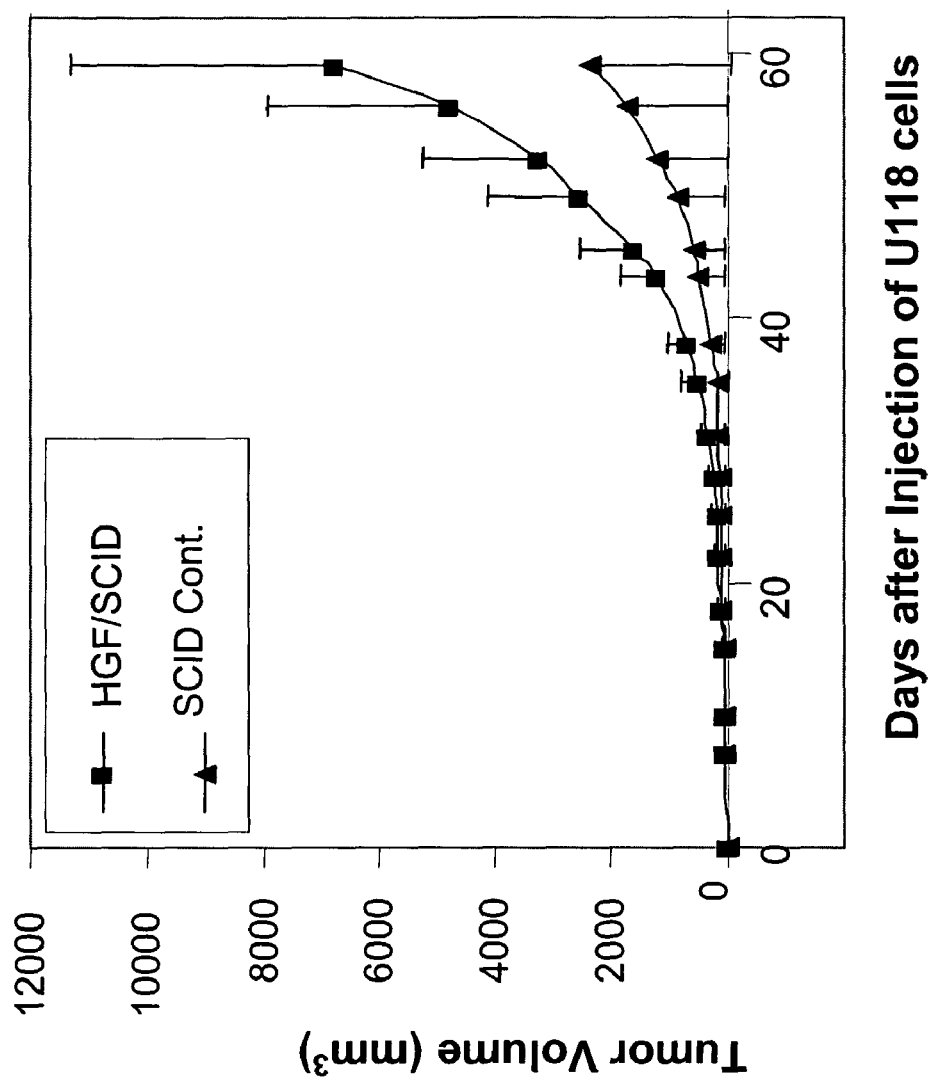
FIG. 7 shows enhanced tumor growth of U118 human tumor cell line xenografts in hHGF Tg scid mice. The study was done as described for FIG. 6. The tumor volumes were averaged from 7 tumors derived from each animal group respectively. (p=0.022; Student's t test:).
Figure 8:
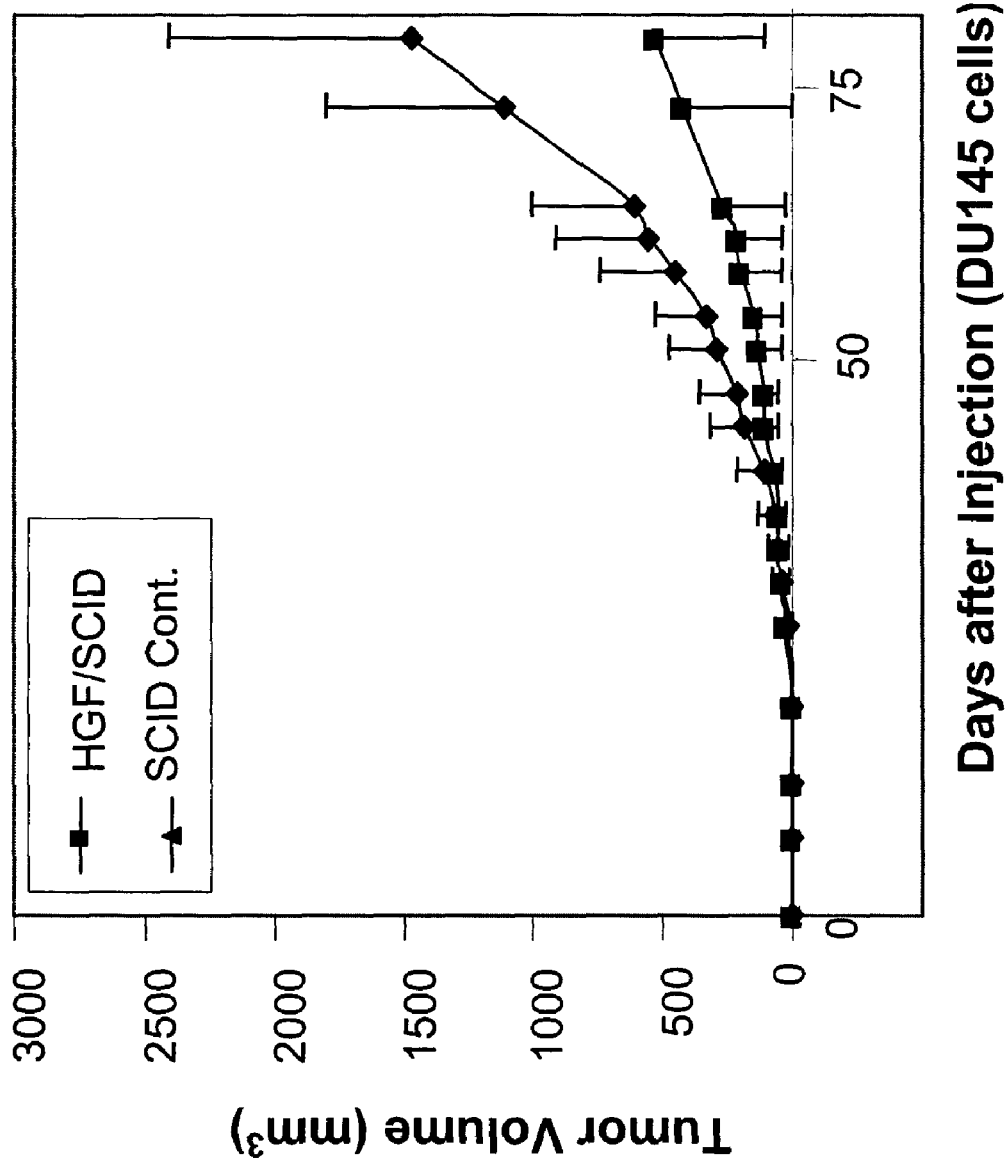
FIG. 8 shows enhanced tumor growth of DU145 human tumor cell line xenografts in hHGF Tg scid mice. The indicated tumor volumes were mean values of 5 tumors derived from each animal group (p=0.039; Student's t test).

The human leiomyosarcoma cell line SK-LMS-1 expresses high level of Met receptor (FIG. 5). Subcutaneously implanted SK-LMS-1 xenografts grew almost threefold faster in hHGF Tg scid mice than in control scid mice (FIG. 6; $0.002<p<0.05$ in Student's t test:). Significant differences (by Student's t test) of similar magnitude were observed with implanted U118 human glioblastoma cells (FIG. 7; $0.022<p<0.05$) and DU145 human prostate cancer cells (FIG. 8; $0.039<p<0.05$), both of which express detectable levels of Met receptor (FIG. 5).

To address whether the tumor growth advantage in the hHGF Tg scid mice was Met receptor-dependent, M14 human melanoma cells were employed, in which Met is undetectable (FIG. 5). As predicted from the foregoing results, the growth of M14 tumor xenografts was indistinguishable in control vs. hHGF Tg scid mice (FIG. 9; $0.25<p<0.05$). It was concluded that ectopically expressed hHGF ligand in scid mice enhanced Met-mediated tumor growth.

Also examined was a subclone, DB-A2, of a Met+ human glioblastoma multiforme tumor (DB-P) that has a unique highly invasive phenotype in response to HGF. From these cells were isolated highly proliferative subclones. The se cells were examined in vitro for proliferation, migration, branching morphogenesis, and anchorage-independent growth, as well as in vivo in a tumorigenesis assays in immune-compromised nude mice. To isolate proliferative subclones from DB-P, cells were plated at low density in DMEM supplemented with HGF for 3 weeks, and fast-growing colonies derived from single cells were subjected to further analysis. The DB-A2 subclone was selected because it was most active in thymidine incorporation assays in response to HGF and showed differences in downstream signaling. DB-P and DB-A2 cells showed comparable levels of Met protein in the absence of ligand, but only DB-P cells showed significant Met down-modulation in response to HGF. Moreover, DB-A2 cells showed low HGF-dependent Erk phosphorylation compared to DB-P cells.

The cells were initially characterized for HGF/SF inducible uPA activity, wound healing-migration, branching morphogenesis, anchorage-independent growth in soft agar, and in vivo for tumorigenicity in nude mice. These characteristics are summarized in Table 2 in comparison with the parental line, DB-P.

TABLE 2

Characterization of DB-AP and DB-A2 cells

| Phenotype | DB-P | DB-A2 |
|---|---|---|
| Migration | ++++ | + |
| Invasion | ++++ | + |
| Branching morphogenesis | ++++ | + |
| uPA-plasmin activity | ++++ | + |
| Proliferation | + | +++ |
| Growth on soft agar | + | +++ |
| Tumorigenic in nude mice | + | +++ |
| MAPK | ++++ | + |
| Myc | + | +++ |

Figure 10:
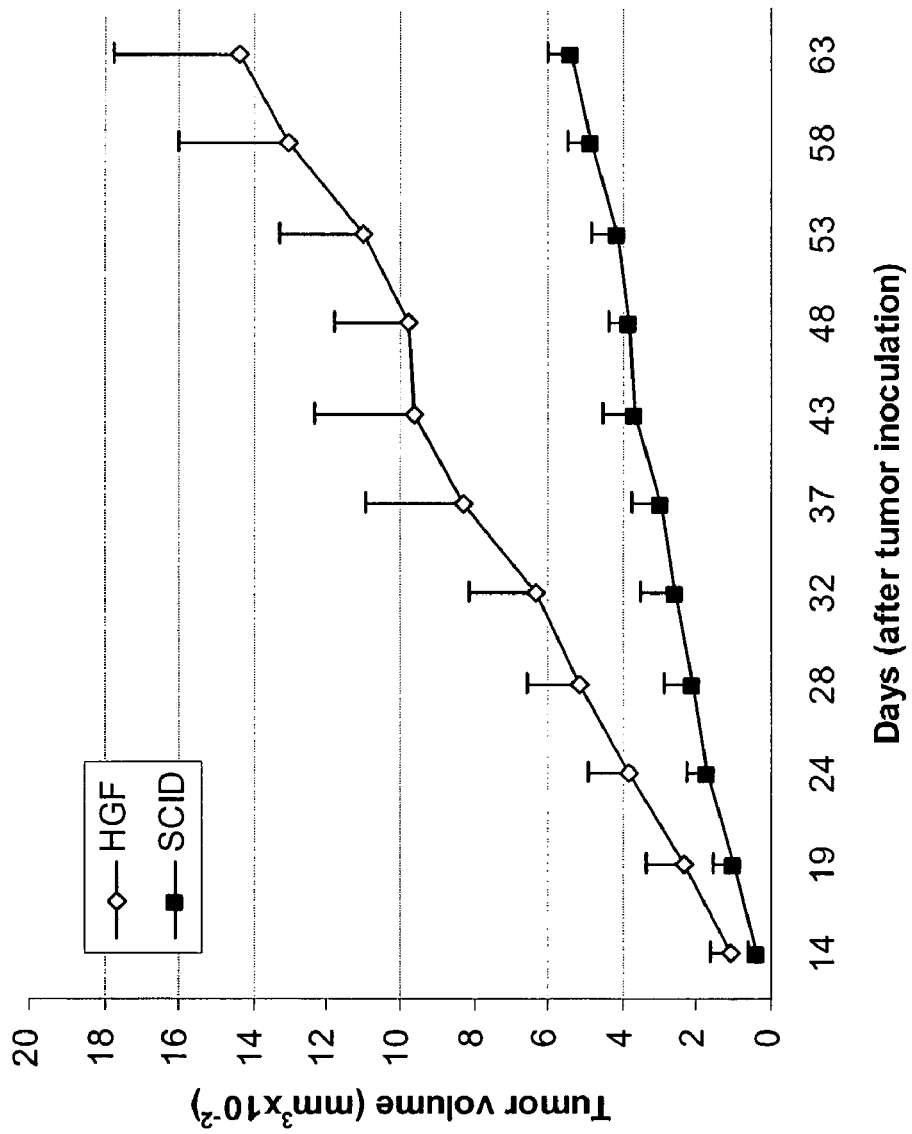
FIG. 10 shows enhanced growth of DB-A2 cells, a subclone of human glioblastoma multiforme in hHGF/SF Tg scid mice compared to C3H/scid mice. Six-week-old female scid or HGF/SF Tg scid mice were injected subcutaneously with cells of the highly proliferative DB-A2 clone ($10^6$/100 μl PBS). Tumor volumes were monitored every 5-6 days (termination at 9 weeks).

The growth of DB-A2 cells were examined in the hHGF Tg mice of the present invention in comparison with growth in C3H scid mice, as with the tumor lines described above. Six-week-old female scid or HGF/SF Tg scid mice were injected subcutaneously with $10^6$ cells, and tumor volumes were monitored every 5-6 days, until mice were euthanized after nine weeks. The results, in FIG. 10, show that the highly proliferating DB-A2 tumor cells grew markedly faster and the tumors reach larger sizes in the hHGF Tg mice.

Discussion of Examples I-V

A suitable animal model serves as a powerful tool in the study of human disease, particularly for obtaining valid preclinical information that is useful in drug discovery. It has been well documented that HGF/SF-Met signaling plays a critical role in the development of human cancer and malignant metastasis. The present invention is based on the targeting of this pathway as an approach to intervening in the development of certain forms of human cancer and in altering the course of tumor malignancy. Drugs or compounds that can inhibit the Met receptor tyrosine kinase activity or block the access of HGF/SF ligand to Met receptor have been sought, and several agents with potential therapeutic values have been identified. However, the systems used to evaluate these agents are not satisfactory for examining human Met expression and activation. Most of the studies in animals that evaluated the activities of these agents employed human tumor cell lines xenografted in athymic nude mice. These animals provide only murine HGF/SF ligand, which may have low affinity for human Met receptor (Kerbel, supra; Bhargava, M et al., *Cell Growth Differ.* 3:11-20 1992). Use of such an incompatible ligand-receptor is expected to yield data that are difficult to interpret. This deficiency in the art prompted the present inventors to develop a mouse model which in which hHGF ligand is available to human tumor cells expressing Met. The present exemplified model is a hHGF Tg mouse that is also immune-compromised by virtue of its being Tg for the scid mutation.

Immune-compromised mouse models allow cells or tissue of foreign origin, such as human tumor xenografts, to grow after subcutaneous, intravenous or other orthotopic introduction. Scid mice have defects in both B and T cell immunity, lack the capability to reject an implanted foreign tissue graft, and have been considered to be one of most useful mouse models for studying human cancer (Bankert, R B et al., *Front Biosci* 7:c44-62, 2002).

The present inventors produced what in effect is a doubly mutant or Tg mouse by combining the scid mutation with a hHGF transgene so that the immune-compromised animals produce the human growth factor, hHGF.

This hHGF Tg scid mouse model allowed the inventors to test human tumor cell lines that either do or do not express the Met receptor to understand the role of hHGF-Met signaling during the growth and development of various human cancers.

Figure 9:
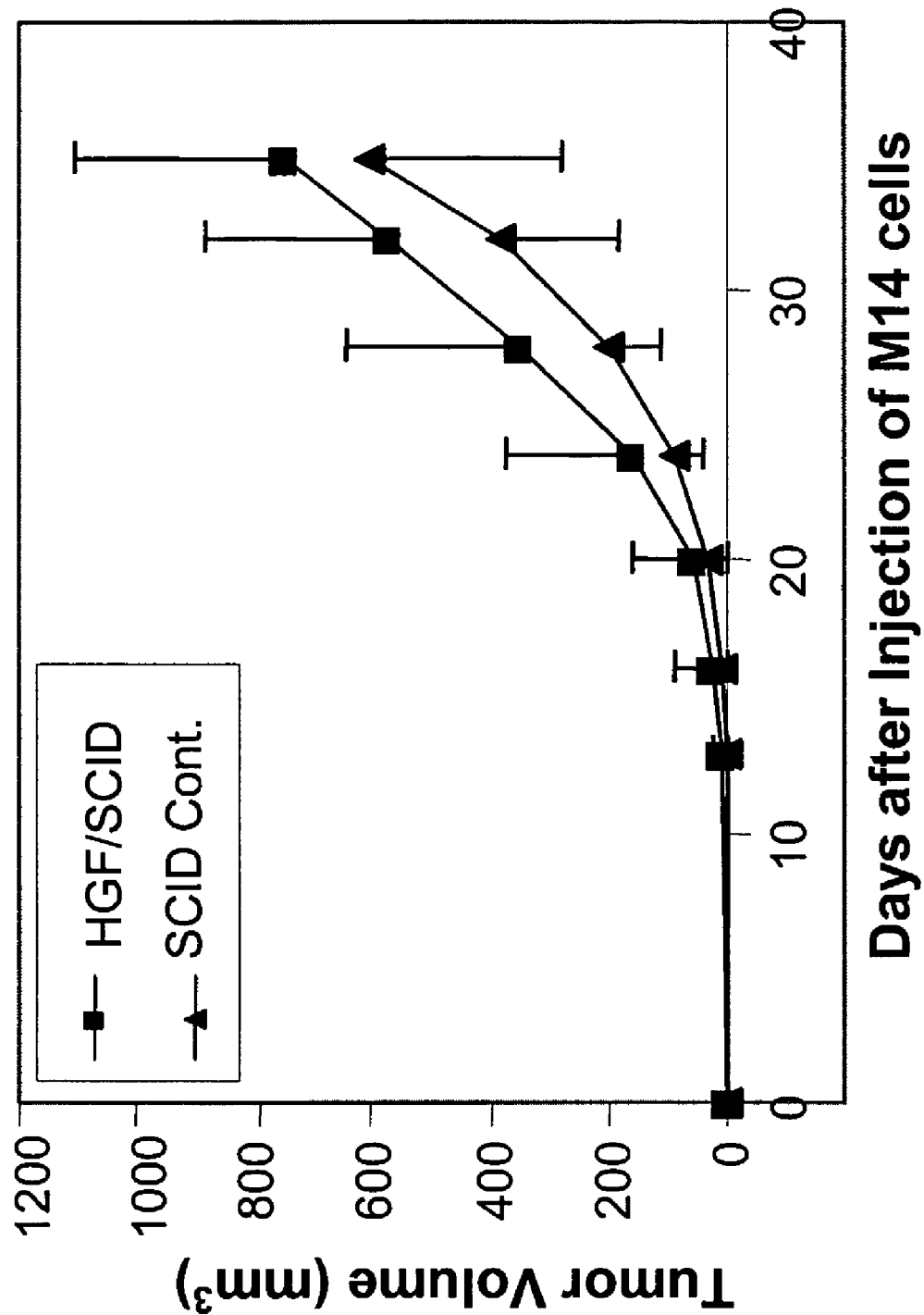
FIG. 9 shows that a Met-neg. cell line M14 has no growth advantage in hHGF Tg scid mice. Met expression in M14 was undetectable. Equal numbers of M14 cells ($10^6$/mouse) were subcutaneously implanted into the backs of the control scid and the hHGF Tg scid mice. Tumor growth was monitored at indicated time points. The means of tumor volumes were plotted (p=0.25; Student's t test). The error bars show standard deviations.

As shown above, the presence of the expressed hHGF transgene significantly enhanced the growth of three different human tumor cell lines of distinct tissue origin: SK-LMS-1 human leiomyosarcoma cells, U118 human glioblastoma cells and DU145 human prostate cancer cells, all of which express Met receptor. When these cells were implanted subcutaneously, the growth rates of the resultant tumors were significantly increased in the hHGF Tg scid mice compared to control scid mice. The enhanced tumor growths of these tumors in the Tg were dependent upon their expression of the human Met gene. This was confirmed by the fact that a tumor cell not expressing Met, the M14 human melanoma, displayed no growth advantage (FIG. 9). Furthermore, a tumor selected to be highly proliferative by in vitro criteria also grew more rapidly under the influence of hHGF in the Tg mice.

Thus, by the addition of the hHGF ligand, which may be either supplanting or supplementing the endogenous murine HGF/SF in scid mice, supported Met-mediated human tumor growth in the mice Compared to the immune compromised scid or athymic nude mice known in the prior art, the hHGF Tg scid mouse model has advantages for studying the HGF/SF-Met pathway because human tumor cells can grow as they are subjected to stimulation with their "natural" ligand, hHGF.

The HGF/SF-Met pathway has also been implicated in the metastatic process in many human cancers. The activation of Met receptor by HGF/SF is considered to be a major stimulus to tumor cells to invade adjacent tissues or to metastasize to remote organs such as lung, liver or bone. It is expected that the constant presence of hHGF ligand will promote metastasis of human tumor cells in vivo.

Moreover, the mice of the present invention can be used to investigate specific types of tumors derived from particular human tissues or organs (such as prostate, breast, kidney, liver) by orthotopic implantation into the homologous mouse tissues or organs, which is expected to provide a more natural microenvironment that better mimics the growth of such tumors in humans. More information on the role of the HGF/SF-Met pathway will also be gained.

EXAMPLE VI

Increased Liver Size in hHGF Transgenic scid/scid Mice

Figure 11:
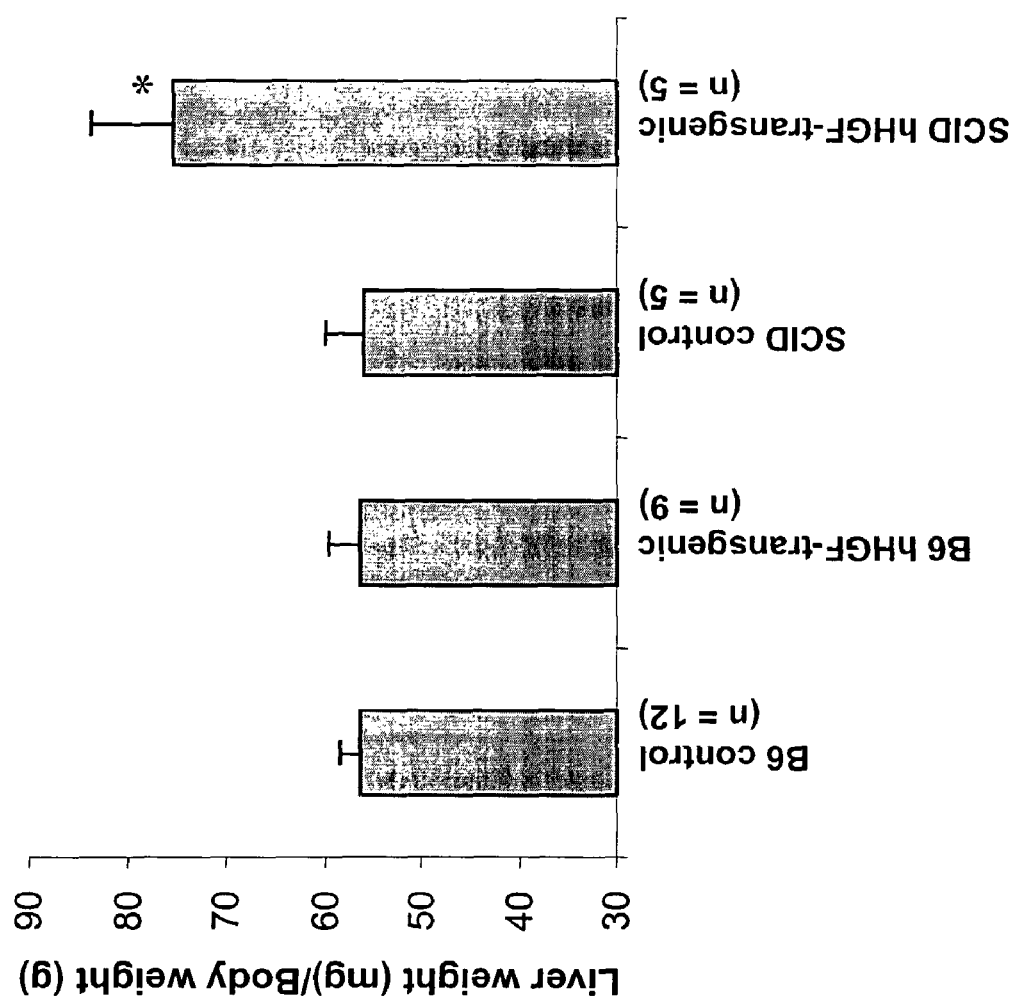
FIG. 11 is a graph showing the effect of expression of the hHGF transgene on mouse liver weight. Liver weight (mg) of the B6 and C3H/scid mice (both normal control and hHGF-transgenic (Tg) was measured and normalized by body weight (g) in litter mates at 8-12 weeks of age. Only hHGF-Tg mice on the C3H/scid background showed such large livers. *p<0.01, compared with other groups.
Figure 12B:
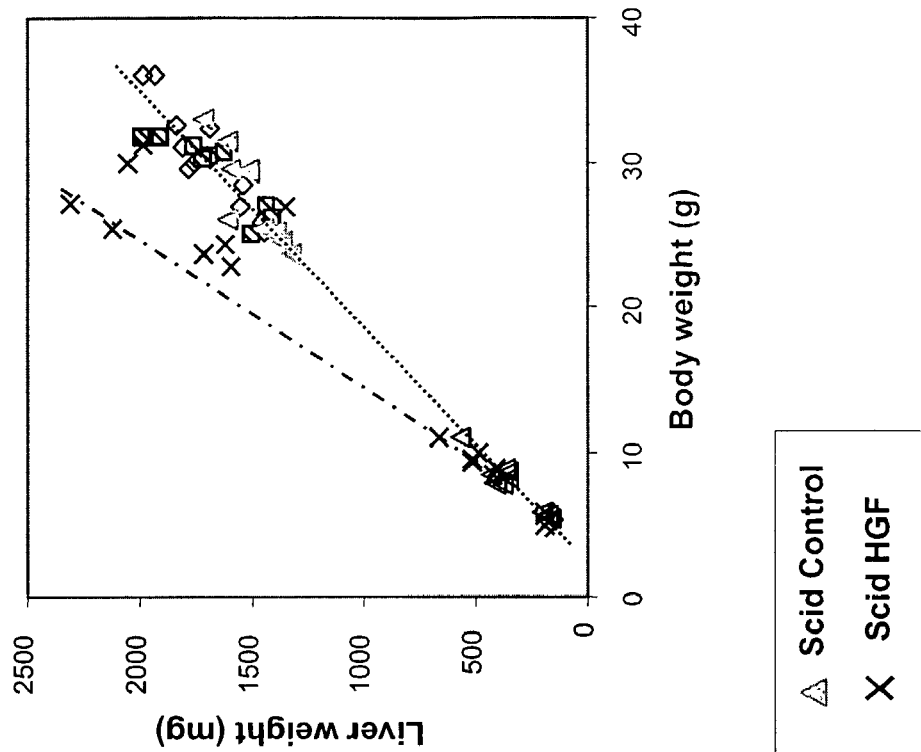
FIGS. 12A and 12B are graphs showing the influence of the age and body weight on mouse liver weight. Body weight (g) and liver weight (mg) of the B6 and C3H/scid mice (both normal control and hHGF Tg) from the same litters were serially measured until 15 weeks of age.
Figure 12A:
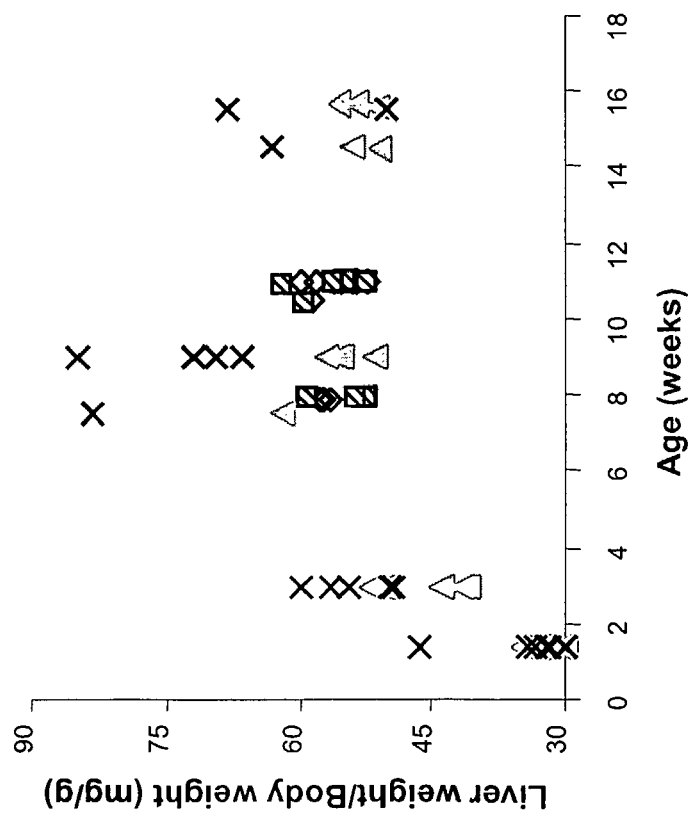
Figure 13:
FIG. 13 shows results of a heparin bead pull-down assay of hHGF. Liver homogenate (1 mg) from the B6 and C3H/scid mice (both normal control and hHGF-transgenic) was incubated with heparin-conjugated beads at 4° C. for 2 hr. After boiling with SDS-PAGE sample buffer, heparin-bound hHGF was separated on an SDS-PAGE gel and detected by Western blot. Rabbit polyclonal anti-hHGF antibody (1:5000 dilution) was used for the detection of hHGF. Culture supernatant of SK-LMS-1 HGF cells was used as positive control. hHGF-Tg scid mice showed high expression of hHGF, whereas hHGF-Tg B6 mice showed faint bands.
Figure 14:
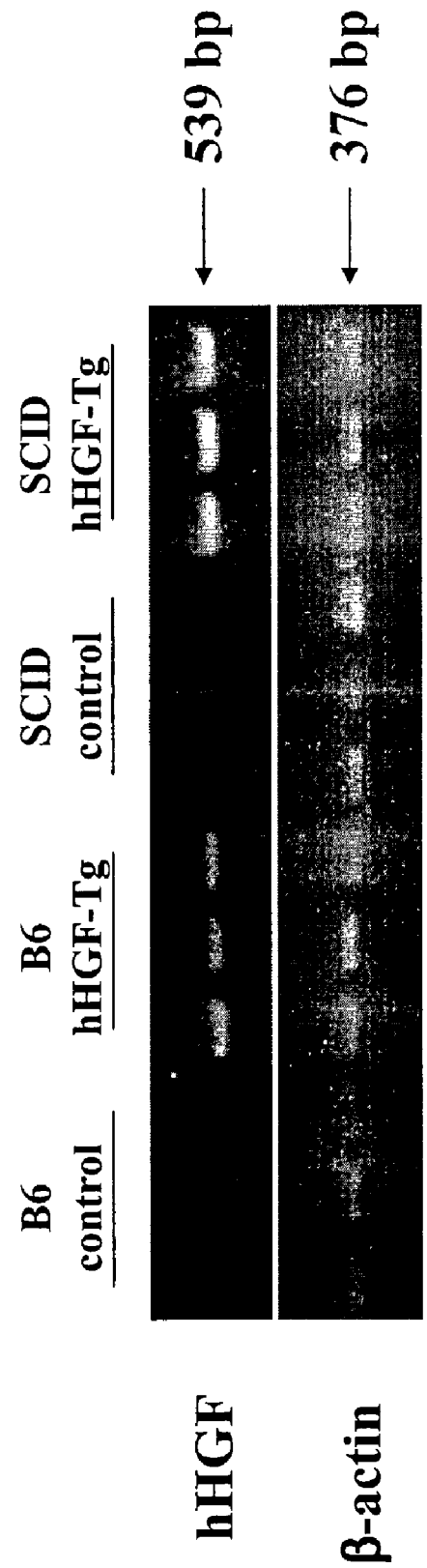
FIG. 14 shows results of RT-PCR analysis of hHGF. Total RNA was purified from liver lysates of normal B6, hHGF-Tg B6, normal C3H/scid, and hHGF-Tg C3H/scid mice respectively. 1 mg total RNA was processed for RT-PCR analysis using hHGF-specific primers. PCR products were separated on 3% agarose gel. β-actin was an internal standard. Expression of hHGF mRNA in the liver was remarkably higher in hHGF-Tg C3H/scid mice than in hHGF-Tg transgenic B6 mice.
Figure 15:
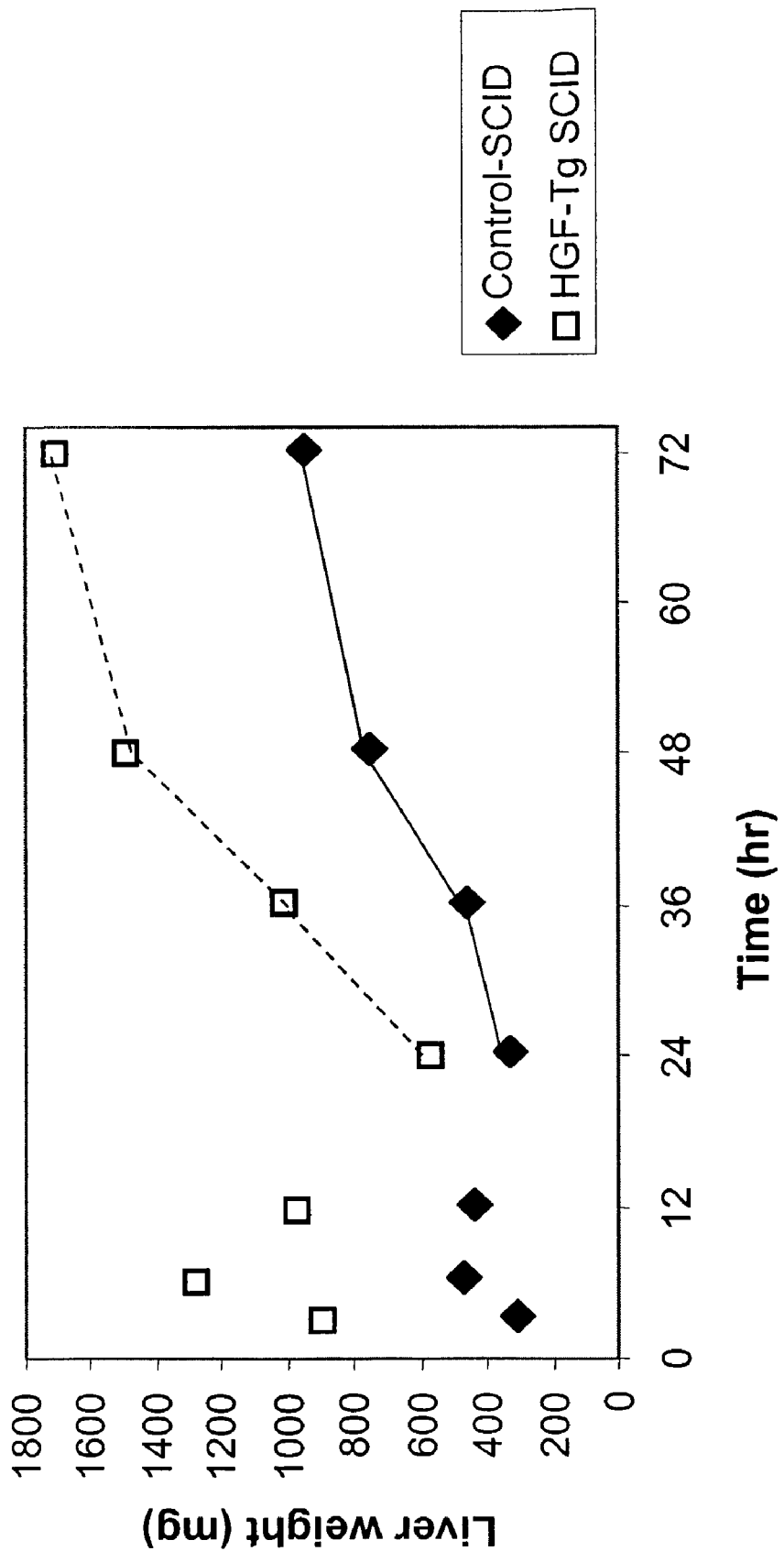
FIG. 15 is a graph showing the effect of hHGF expression on liver regeneration. Mice were serially sacrificed after a partial (⅔) hepatectomy, and the remnant liver was weighed. Livers of hHGF-Tg C3H scid mice regenerated more rapidly than did those of control C3H scid.

Livers of the mice produced as described above were examined. These animals were found to have an markedly enlarged yet normal livers compared with the age-matched control mice or hHGF-transgenic mice on a different genetic background (C57BL/6 or "B6"). The results are shown in FIGS. 11 and 12A-12B). Expression of the hHGF transgene was very high in the liver only in hHGF-transgenic/scid C3H mice but not in hHGF-transgenic/B6 mice (FIGS. 13 and 14).

It was concluded that hHGF is a growth factor that can result in a massive increase in size of a mouse liver. As shown in FIG. 14 these hHGF-transgenic/scid mice also showed accelerated liver regeneration. Therefore, hHGF can regulate liver size without having any discernible effects on the growth or size of other tissues and organs in the same animals.

HGF has already been considered as a therapeutic agent for liver diseases such as cirrhosis or for the enhancement of hepatocyte growth and viability after liver transplantation. However, this is the first discovery that the presence of hHGF can increase size of a normal mouse liver. Because liver regeneration is stimulated to the extent of reconstituting an enlarged "normal" liver in these animals, it is concluded that hHGF is at least one component that responsible for determining normal liver size and may, at the same time, be used as a drug or stimulatory agent to increase the size of normal liver in vivo.

Thus the present animals are useful for growing enlarged murine livers. Furthermore, if human liver tissue is implanted into such mice, it will experience a similar growth stimulation so that human hepatocytes and or liver tissue fragments may be harvested from such animals and transplanted into humans to help restore function in subjects suffering from liver disease that results in dysfunction or death of hepatocytes.

The entire disclosure of all patent applications, patents and publications, cited above and below and in the figures are hereby incorporated by reference in their entirety, whether specifically incorporated above or not.

From the foregoing description, one skilled in the art can easily ascertain the essential characteristics of this invention, and without departing from the spirit and scope thereof, can make changes and modifications of the invention to adapt it to various usage and conditions. Without further elaboration, it is believed that one skilled in the art can, using the preceding description, utilize the present invention to its fullest extent. The preceding preferred specific embodiments are, therefore, to be construed as merely illustrative, and not limiting of the remainder of the disclosure in any way.

What is claimed is:

1. A transgenic, immunocompromised mouse of the C3H strain whose genome comprises a DNA sequence encoding human hepatocyte growth factor (hHGF) which is operably linked to an expression control sequence, wherein the mouse comprises human Met (hMet) tumor cells, wherein the expression of the hHGF in the mouse stimulates increased growth of the human tumor cells in the mouse as compared to growth of the same tumor cells introduced into an immunocompromised mouse whose genome is not transgenic for hHGF.

2. The transgenic mouse of claim 1, in which the stimulation results in an increased rate of growth of said human tumor cells of 2.1- to 6.0-fold compared to growth of the same tumor cells introduced into an immunocompromised mouse whose genome is not transgenic for hHGF.

3. The transgenic mouse of claim 1, which is a scid mouse.

4. The transgenic mouse of claim 1, wherein the hHGF is wild type hHGF.

5. The transgenic mouse of claim 1, wherein the DNA sequence encodes an active fragment or variant of hHGF.

6. The transgenic mouse of claim 1, wherein the expression control sequence comprises a constitutive promoter.

7. The transgenic mouse of claim 1, wherein the expression control sequence comprises a tissue-specific promoter.

8. The transgenic mouse of claim 1, wherein the expression control sequence comprises an inducible/repressible promoter or control element.

9. The transgenic mouse of claim 1, wherein the expression control sequence comprises a mouse metallothionein-1 (MT) promoter.

10. The transgenic mouse of claim 1, which is heterozygous or hemizygous for the hHGF.

11. The transgenic mouse of claim 1, which is homozygous for the hHGF DNA.

12. The transgenic mouse of claim 1, which is fertile.

13. The transgenic mouse of claim 1, which is a scid mouse homozygous for the hHGF DNA, in which the hHGF coding sequence is operably linked to a mouse MT promoter.

14. The transgenic mouse of claim 1, wherein the human tumor cell is from the cell line SK-LMS-I, U118, DU145, DBTRG-05MG or DB-A2.

15. The transgenic mouse of claim 1, wherein the human tumor cell is a hepatocyte.

16. The transgenic mouse of claim 1, wherein the DNA encoding said hHGF was introduced into the animal, or an ancestor thereof, at an embryonic stage.

17. A method for growing human Met+ cells in vivo in a mouse, comprising introducing human Met+ tumor cells into a transgenic, immunocompromised mouse of the C3H strain whose genome comprises a DNA sequence encoding human hepatocyte growth factor (hHGF) which is operably linked to an expression control sequence, and wherein expression of hHGF permits said cells to grow.

18. The method of claim 17, wherein said tumor cells grow into a solid tumor in said mouse.

19. The method of claim 17, wherein said tumor cells are leukemia or lymphoma cells.

20. The method of claim 17, wherein said tumor cells migrate and metastasize in said mouse.

21. The method of claim 17, wherein said human tumor cells are liver cells.

22. A method for testing an agent for its ability to inhibit growth or metastasis of a Met+ human tumor, comprising exposing a transgenic immunocompromised mouse of the C3H strain to a test agent, before, concurrently with, or after implantation of Met+ tumor cells, wherein the genome of the mouse comprises a DNA sequence encoding human hepatocyte growth factor (hHGF) which is operably linked to an expression control sequence.

23. The method of claim 22, wherein the test agent is an inhibitor of hMet and/or hHGF expression and/or activity.

24. The method of claim 23, wherein the inhibitor inhibits Met-mediated tyrosine kinase activity.

25. The method of claim 22, wherein the test agent is a small molecule.

26. The method of claim 22, wherein the test agent is an antibody.

27. The method of claim 26, wherein the antibody is specific for hHGF or hMet.

28. The method of claim 22, wherein the test agent is a nucleic acid which inhibits expression of hMet and/or hHGF.

29. A method for evaluating the effect of a test agent or treatment as a potential therapy for a Met+ human tumor, comprising administering a test agent or treatment to a transgenic mouse of claim 1, and comparing the growth or metastasis of implanted tumor cells to the growth or metastasis of Met+ tumor cells in a second mouse of claim 1 that has not been administered a test agent or treatment.

30. The method of claim 29, wherein the test agent or treatment comprises radiotherapy photodynamic therapy, immunotherapy or gene therapy.

31. A method for producing the transgenic mouse of claim 1, comprising incorporating into the genome of an immunocompromised C3H mouse, in at least one site, a polynucleotide encoding hHGF which is operably linked to an expression control sequence, wherein the expression of the polynucleotide in the mouse is effective to support the growth or survival of Met+ human tumor cells or tissue, and implanting human Met+ tumor cells into the mouse.

32. The method of claim 31, wherein prior to human Met+ tumor implantation, the transgenic mouse is backcrossed to a scid/scid mouse for a sufficient number of generations to obtain a transgenic mouse which is congenic for hHGF on the scid background, wherein expression of the polynucleotide in the transgenic mouse is effective to support the growth of Met+human tumor cells or tissue.

* * * * *

UNITED STATES PATENT AND TRADEMARK OFFICE
CERTIFICATE OF CORRECTION

PATENT NO. : 7,968,762 B2  
APPLICATION NO. : 11/571947  
DATED : June 28, 2011  
INVENTOR(S) : Vande Woude et al.

It is certified that error appears in the above-identified patent and that said Letters Patent is hereby corrected as shown below:

On the cover page, in the Title (54) delete "IMMUNE-COMPROMISED TRANSGENIC MICE EXPRESSING HUMAN HEPATOCYTE GROWTH FACTOR (HHGF)" and replace with -- IMMUNE-COMPROMISED TRANSGENIC MICE EXPRESSING HUMAN HEPATOCYTE GROWTH FACTOR (hHGF) --

On the cover page in the PCT filed (22), delete "Jul. 12, 2005" and replace with -- Jul. 13, 2005 --

On the cover page, on line 7 of the Abstract (57), delete "hHGF/SE" and replace with -- hHGF/SF --

Signed and Sealed this  
Thirty-first Day of January, 2012

David J. Kappos  
*Director of the United States Patent and Trademark Office*

UNITED STATES PATENT AND TRADEMARK OFFICE
CERTIFICATE OF CORRECTION

PATENT NO.        : 7,968,762 B2                                         Page 1 of 1
APPLICATION NO.   : 11/571947
DATED             : June 28, 2011
INVENTOR(S)       : Vande Woude et al.

It is certified that error appears in the above-identified patent and that said Letters Patent is hereby corrected as shown below:

On the cover page, Item (54) and at Column 1, lines 1-3, in the Title delete
"IMMUNE-COMPROMISED TRANSGENIC MICE EXPRESSING HUMAN HEPATOCYTE GROWTH FACTOR (HHGF)" and replace with
-- IMMUNE-COMPROMISED TRANSGENIC MICE EXPRESSING HUMAN HEPATOCYTE GROWTH FACTOR (hHGF) --

On the cover page in the PCT filed (22), delete "Jul. 12, 2005" and replace with -- Jul. 13, 2005 --

On the cover page, on line 7 of the Abstract (57), delete "hHGF/SE" and replace with -- hHGF/SF --

This certificate supersedes the Certificate of Correction issued January 31, 2012.

Signed and Sealed this
Twenty-first Day of February, 2012

David J. Kappos
*Director of the United States Patent and Trademark Office*